(12) United States Patent
Lee et al.

US009725533B2

(10) Patent No.: US 9,725,533 B2
(45) Date of Patent: Aug. 8, 2017

(54) METALLOCENE COMPOUND, A CATALYST COMPOSITION COMPRISING THE SAME, AND A METHOD OF PREPARING AN OLEFINIC POLYMER BY USING THE SAME

(71) Applicant: LG CHEM, LTD., Seoul (KR)

(72) Inventors: Yong Ho Lee, Daejeon (KR); Eun Kyoung Song, Daejeon (KR); Kyung Jin Cho, Daejeon (KR); Ki Soo Lee, Daejeon (KR); Se Young Kim, Daejeon (KR); Sung Min Lee, Daejeon (KR); Hyuck Ju Kwon, Daejeon (KR); Yi Young Choi, Daejeon (KR); Heon Yong Kwon, Daejeon (KR); Min Seok Cho, Daejeon (KR); Dae Sik Hong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/908,450

(22) PCT Filed: Oct. 11, 2013

(86) PCT No.: PCT/KR2013/009114
§ 371 (c)(1),
(2) Date: Jan. 28, 2016

(87) PCT Pub. No.: WO2015/016422
PCT Pub. Date: Feb. 5, 2015

(65) Prior Publication Data
US 2016/0168281 A1 Jun. 16, 2016

(30) Foreign Application Priority Data
Aug. 1, 2013 (KR) .................. 10-2013-0091622

(51) Int. Cl.
C07F 17/00 (2006.01)
C08F 4/6592 (2006.01)
C08F 10/00 (2006.01)
C08F 10/02 (2006.01)
C08F 4/659 (2006.01)
B01J 31/12 (2006.01)
C07F 7/00 (2006.01)
C07F 7/08 (2006.01)

(52) U.S. Cl.
CPC .............. *C08F 10/02* (2013.01); *B01J 31/12* (2013.01); *C07F 7/00* (2013.01); *C07F 7/082* (2013.01); *C07F 17/00* (2013.01); *C08F 4/65908* (2013.01); *C08F 4/65912* (2013.01); *C08F 4/65927* (2013.01); *C08F 10/00* (2013.01); *C08F 2420/06* (2013.01)

(58) Field of Classification Search
CPC .............. C08F 4/65927; C08F 4/65908; C08F 4/65912; C08F 10/00
See application file for complete search history.

(56) References Cited

U.S. PATENT DOCUMENTS

| 5,064,802 A | 11/1991 | Stevens et al. |
| 6,861,485 B2 | 3/2005 | Wang |
| 7,026,494 B1 | 4/2006 | Yang et al. |
| 2003/0229188 A1 | 12/2003 | Nagy et al. |
| 2006/0199726 A1 | 9/2006 | Nagy |
| 2012/0123078 A1 | 5/2012 | Lee et al. |

FOREIGN PATENT DOCUMENTS

| JP | 2008531838 A | 8/2008 |
| KR | 102000062706 A | 10/2000 |
| KR | 1020020034193 | 5/2002 |
| KR | 1020060021476 A | 3/2004 |
| KR | 1020050024287 A | 3/2005 |
| KR | 1020060031633 | 4/2006 |
| KR | 20100028317 A | 3/2010 |
| KR | 1020110013286 | 2/2011 |
| KR | 20120087706 A | 8/2012 |
| WO | 92/05203 A1 | 4/1992 |
| WO | 94/07928 A1 | 4/1994 |
| WO | 2009/032048 A1 | 3/2009 |
| WO | 2009/032049 A1 | 3/2009 |
| WO | 2009/032051 A1 | 3/2009 |

*Primary Examiner* — Caixia Lu
(74) *Attorney, Agent, or Firm* — Dentons US LLP

(57) ABSTRACT

The present invention relates to a novel metallocene compound, a catalyst composition including the same, and a method of preparing an olefinic polymer by using the same. The metallocene compound according to the present invention and the catalyst composition comprising the same can be used for producing olefinic polymers, have outstanding polymerizing ability, and can produce olefinic polymers of ultra high molecular weight. In particular, when the metallocene compound according to the present invention is employed, an olefinic polymer of ultra high molecular weight can be obtained because it shows high polymerization activity even when it is supported on a carrier and maintains high activity even in the presence of hydrogen because of its low hydrogen reactivity.

15 Claims, No Drawings

METALLOCENE COMPOUND, A CATALYST COMPOSITION COMPRISING THE SAME, AND A METHOD OF PREPARING AN OLEFINIC POLYMER BY USING THE SAME

This application is a National Stage Entry of International Application No. PCT/KR2013/009114, filed Oct. 11, 2013, and claims the benefit of and priority to Korean Application No. 10-2013-0091622, filed Aug. 1, 2013, each of which are hereby incorporated by reference in their entirety for all purposes as if fully set forth herein.

BACKGROUND OF THE INVENTION (a) Field of the Invention

The present invention relates to a novel metallocene compound, a catalyst composition including the same, and a method of preparing an olefinic polymer by using the same. This application claims priority to and the benefit of Korean Patent Application 10-2013-0091622 filed in the Korean Intellectual Property Office on Aug. 1, 2013, the entire content of which is incorporated herein by reference.

(b) Description of the Related Art

Dow Co. had presented [Me$_2$Si(Me$_4$C$_5$)NtBu]TiCl$_2$ (Constrained-Geometry Catalyst, hereinafter 'CGC') in the early 1990's (U.S. Pat. No. 5,064,802), the superior aspects of the CGC to prior known metallocene catalysts in copolymerization reaction of ethylene and α-olefin can be largely summarized into two ways as follows: (1) it shows high activity even in high polymerization temperature and forms a polymer of high molecular weight, (2) the copolymerizing ability of α-olefin such as 1-hexene and 1-octene which have large steric hindrance is also very excellent. In addition, as various characteristics in the polymerization reaction of the CGC became gradually known, there have been many efforts to synthesize derivatives of the same for using it as a polymerization catalyst in the academic world and the industrial world.

Group 4 transition metal compound which has one or two cyclopentadienyl groups as the ligand can be used as a catalyst for olefin polymerization by activating the same with methylaluminoxane or a boron compound. Such catalyst shows unique characteristics that traditional Ziegler-Natta catalyst cannot realize.

Namely, the polymer obtained by using such catalyst has narrow molecular weight distribution and more good reactivity to the second monomer such as α-olefin or cycloolefin, and the second monomer distribution in the polymer is even. Furthermore, it is possible to control the stereoselectivity of the polymer in the polymerization of α-olefin by changing the substituent of the cyclopentadienyl ligand in the metallocene catalyst, and the degree of copolymerization, the molecular weight, and the distribution of the second monomer can be easily controlled in copolymerization of ethylene and other olefins.

Meanwhile, since the metallocene catalyst is more expensive than Ziegler-Natta catalyst, it must have good activity for its economic value. If it has good reactivity to the second monomer, there is an advantage of that the polymer including large content of the second monomer can be obtained by using only small amount of the second monomer.

As the results that many researchers have studied various catalysts, it is proved that generally a bridged catalyst has good reactivity to the second monomer. The bridged catalyst developed until now can be classified into three types according the type of the bridge. The first type is the catalyst of which two cyclopentadienyl ligands are connected with an alkylene dibridge by the reaction of an electrophile like an alkyl halide and indene or fluorene, the second type of the silicone-bridged catalyst of which the ligands are connected with —SiR$_2$—, and the third type is the methylene-bridged catalyst which is obtained by the reaction of fulvene and indene or fluorene.

However, very few catalysts have been being applied in practice in commercial factories among above attempts, and thus the preparation of catalyst showing more improved polymerization performance is still required.

SUMMARY OF THE INVENTION

To resolve the problems of prior technology, it is an aspect of the present invention to provide a metallocene compound that is superior in activity and can form an olefinic polymer having high molecular weight, a catalyst composition including the same, a method of preparing an olefinic polymer by using the same, and an olefinic polymer prepared by using the same.

Specifically, it is an aspect of the present invention to provide a metallocene compound which shows high polymerization activity even when it is supported on a carrier and maintains high activity even in the presence of hydrogen because of its low hydrogen reactivity and can prepare an olefinic polymer of ultra high molecular weight, a catalyst composition including the same, a method of preparing an olefinic polymer by using the same, and an olefinic polymer prepared by using the same.

The present invention provides a metallocene compound represented by the following Chemical Formula 1:

[Chemical Formula 1]

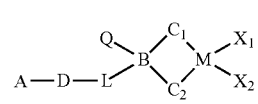

In Chemical Formula 1,

A is hydrogen, a halogen, a $C_1$-$C_{20}$ alkyl group, a $C_2$-$C_{20}$ alkenyl group, a $C_6$-$C_{20}$ aryl group, a $C_7$-$C_{20}$ alkylaryl group, a $C_7$-$C_{20}$ arylalkyl group, a $C_1$-$C_{20}$ alkoxy group, a $C_2$-$C_{20}$ alkoxyalkyl group, a $C_3$-$C_{20}$ heterocycloalkyl group, or a $C_5$-$C_{20}$ heteroaryl group;

D is —O—, —S—, —N(R)—, or —Si(R)(R')—, wherein R and R' are same or different each other, and are independently hydrogen, a halogen, a $C_1$-$C_{20}$ alkyl group, a $C_2$-$C_{20}$ alkenyl group, or a $C_6$-$C_{20}$ aryl group;

L is a $C_1$-$C_{10}$ linear or branched alkylene group;

B is carbon, silicon, or germanium;

Q is hydrogen, a halogen, a $C_1$-$C_{20}$ alkyl group, a $C_2$-$C_{20}$ alkenyl group, a $C_6$-$C_{20}$ aryl group, a $C_7$-$C_{20}$ alkylaryl group, or a $C_7$-$C_{20}$ arylalkyl group;

M is a group 4 transition metal;

$X_1$ and $X_2$ are, same to or different from each other, independently hydrogen, a halogen, a $C_1$-$C_{20}$ alkyl group, a $C_2$-$C_{20}$ alkenyl group, a $C_6$-$C_{20}$ aryl group, a nitro group, an amido group, a $C_1$-$C_{20}$ alkylsilyl group, a $C_1$-$C_{20}$ alkoxy group, or a $C_1$-$C_{20}$ sulfonate group;

$C_1$ is represented by any one of the following Chemical Formula 2a and Chemical Formula 2b; and $C_2$ is represented by the following Chemical Formula 3:

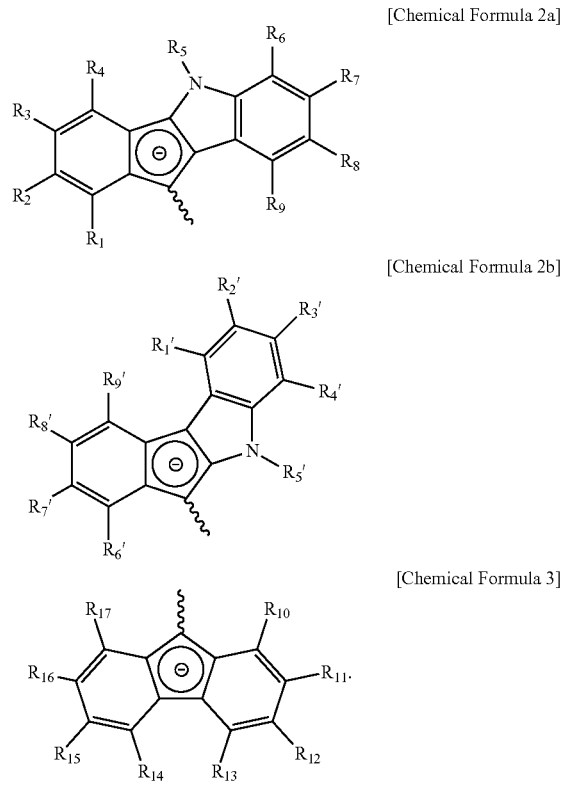

[Chemical Formula 2a]

[Chemical Formula 2b]

[Chemical Formula 3]

In Chemical Formulae 2a, 2b and 3, $R_1$ to $R_{17}$ and $R_1'$ to $R_9'$ are, same to or different from each other, independently hydrogen, a halogen, a $C_1$-$C_{20}$ alkyl group, a $C_2$-$C_{20}$ alkenyl group, a $C_1$-$C_{20}$ alkylsilyl group, a $C_1$-$C_{20}$ silylalkyl group, a $C_1$-$C_{20}$ alkoxysilyl group, a $C_1$-$C_{20}$ alkoxy group, a $C_6$-$C_{20}$ aryl group, a $C_7$-$C_{20}$ alkylaryl group, or a $C_7$-$C_{20}$ arylalkyl group, wherein two or more adjacent groups among $R_{10}$ to $R_{17}$ may form a substituted or unsubstituted aliphatic or aromatic ring by being connected together.

The present invention also provides a catalyst composition including the metallocene compound.

The present invention also provides a method of preparing an olefinic polymer including the step of polymerizing olefinic monomers in the presence of the catalyst composition.

The present invention also provides an olefinic polymer prepared by the preparation method.

The metallocene compound according to the present invention or the catalyst composition comprising the same can be used for producing olefinic polymers, have outstanding activity, and can produce olefinic polymers of high molecular weight.

In particular, when the metallocene compound according to the present invention is employed, an olefinic polymer of ultra high molecular weight can be obtained because it shows high polymerization activity even when it is supported on a carrier and maintains high activity even in the presence of hydrogen because of its low hydrogen reactivity.

Furthermore, the activity of the catalyst can be maintained for a long residence time in a reactor because of its long life time.

DETAILED DESCRIPTION OF THE EMBODIMENTS

In the present invention, the terms "the first", "the second", and the like are used for explaining various components and said terms are only used for distinguishing one component from the other components.

Furthermore, the terms used in this description are just for explaining exemplary examples and it is not intended to restrict the present invention. The singular expression may include the plural expression unless it is differently expressed contextually. It must be understood that the terms such as "include", "equip", and "have" in the present description are only used for designating the existence of characteristics taken effect, numbers, steps, components, or combinations thereof, and do not exclude the existence or the possibility of addition of one or more different characteristics, numbers, steps, components of combinations thereof beforehand.

The present invention can be variously modified and have various forms, and specific examples of the present invention are explained in this description. However, it is not intended to limit the present invention to the specific examples and it must be understood that the present invention includes every modifications, equivalents, or replacements included in the idea and technical scope of the present invention.

Hereinafter, the present invention is explained in more detail.

The metallocene compound according to the present invention is characterized in that it is represented by the following Chemical Formula 1.

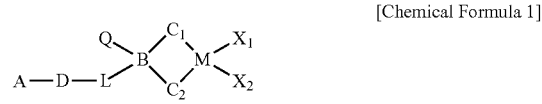

[Chemical Formula 1]

In Chemical Formula 1,

A is hydrogen, a halogen, a $C_1$-$C_{20}$ alkyl group, a $C_2$-$C_{20}$ alkenyl group, a $C_6$-$C_{20}$ aryl group, a $C_7$-$C_{20}$ alkylaryl group, a $C_7$-$C_{20}$ arylalkyl group, a $C_1$-$C_{20}$ alkoxy group, a $C_2$-$C_{20}$ alkoxyalkyl group, a $C_3$-$C_{20}$ heterocycloalkyl group, or a $C_5$-$C_{20}$ heteroaryl group;

D is —O—, —S—, —N(R)—, or —Si(R)(R')—, wherein R and R' are same or different each other, and are independently hydrogen, a halogen, a $C_1$-$C_{20}$ alkyl group, a $C_2$-$C_{20}$ alkenyl group, or a $C_6$-$C_{20}$ aryl group;

L is a $C_1$-$C_{10}$ linear or branched alkylene group;

B is carbon, silicon, or germanium;

Q is hydrogen, a halogen, a $C_1$-$C_{20}$ alkyl group, a $C_2$-$C_{20}$ alkenyl group, a $C_6$-$C_{20}$ aryl group, a $C_7$-$C_{20}$ alkylaryl group, or a $C_7$-$C_{20}$ arylalkyl group;

M is a group 4 transition metal;

$X_1$ and $X_2$ are, same to or different from each other, independently hydrogen, a halogen, a $C_1$-$C_{20}$ alkyl group, a $C_2$-$C_{20}$ alkenyl group, a $C_6$-$C_{20}$ aryl group, a nitro group, an amido group, a $C_1$-$C_{20}$ alkylsilyl group, a $C_1$-$C_{20}$ alkoxy group, or a $C_1$-$C_{20}$ sulfonate group;

$C_1$ is represented by any one of the following Chemical Formula 2a and Chemical Formula 2b; and $C_2$ is represented by the following Chemical Formula 3:

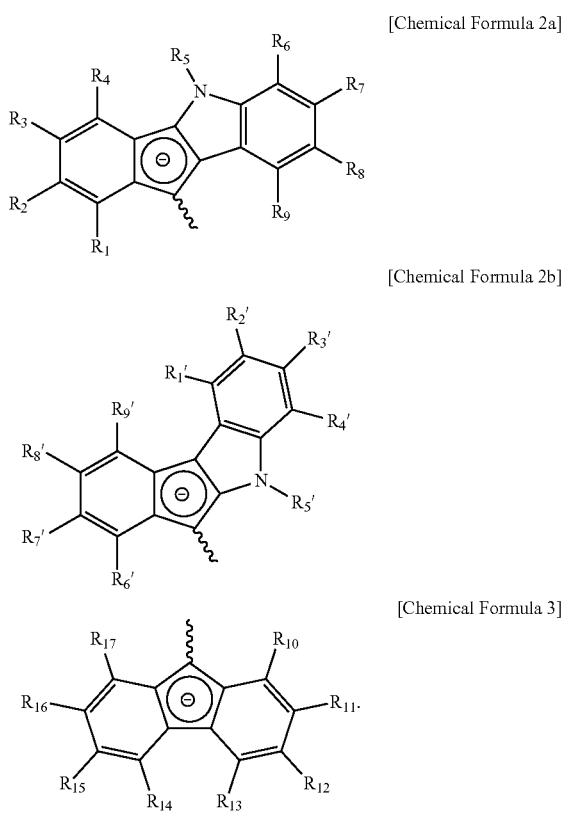

[Chemical Formula 2a]

[Chemical Formula 2b]

[Chemical Formula 3]

In Chemical Formulae 2a, 2b and 3, $R_1$ to $R_{17}$ and $R_1'$ to $R_9'$ are, same to or different from each other, independently hydrogen, a halogen, a $C_1$-$C_{20}$ alkyl group, a $C_2$-$C_{20}$ alkenyl group, a $C_1$-$C_{20}$ alkylsilyl group, a $C_1$-$C_{20}$ silylalkyl group, a $C_1$-$C_{20}$ alkoxysilyl group, a $C_1$-$C_{20}$ alkoxy group, a $C_6$-$C_{20}$ aryl group, a $C_7$-$C_{20}$ alkylaryl group, or a $C_7$-$C_{20}$ arylalkyl group, wherein 2 or more adjacent groups among $R_{10}$ to $R_{17}$ may form a substituted or unsubstituted aliphatic or aromatic ring by being connected together.

In the metallocene compound of the present invention, the substituents of Chemical Formula 1 are more specifically explained as follows.

The $C_1$-$C_{20}$ alkyl group may include a linear or branched alkyl group, and, specifically, it may be methyl group, ethyl group, propyl group, isopropyl group, n-butyl group, tert-butyl group, pentyl group, hexyl group, heptyl group, octyl group, and the like, however, it is not limited to them.

The $C_2$-$C_{20}$ alkenyl group may include a linear or branched alkenyl group, and, specifically, it may be allyl group, ethenyl group, propenyl group, butenyl group, pentenyl group, and the like, however, it is not limited to them.

The $C_6$-$C_{20}$ aryl group may include a single ring aryl group or a condensed ring aryl group, and, specifically, it may be phenyl group, biphenyl group, naphthyl group, phenanthrenyl group, fluorenyl group, and the like, however, it is not limited to them.

The $C_5$-$C_{20}$ heteroaryl group may include a single ring heteroaryl group or a condensed ring heteroaryl group, and, specifically, it may be carbazolyl group, pyridyl group, quinoline group, isoquinoline group, thiophenyl group, furanyl group, imidazole group, oxazolyl group, thiazolyl group, triazine group, tetrahydropyranyl group, tetrahydrofuranyl group, and the like, however, it is not limited to them.

The $C_1$-$C_{20}$ alkoxy group may be methoxy group, ethoxy group, phenyloxy group, cyclohexyloxy group, and the like, however, it is not limited to them.

The Group 4 transition metal may be titanium, zirconium, hafnium, and the like, however, it is not limited to them.

In the metallocene compound according to the present invention, it is preferable that $R_1$ to $R_{17}$ and $R_1'$ to $R_9'$ in Chemical Formulae 2a, 2b and 3 are independently hydrogen, methyl group, ethyl group, propyl group, isopropyl group, n-butyl group, tert-butyl group, pentyl group, hexyl group, heptyl group, octyl group, phenyl group, a halogen group, trimethylsilyl group, triethylsilyl group, tripropylsilyl group, tributylsilyl group, triisopropylsilyl group, trimethylsilylmethyl group, methoxy group, or ethoxy group, however, it is not limited to them.

In the metallocene compound according to the present invention, it is preferable that L in Chemical Formula 1 is a $C_4$-$C_8$ linear or branched alkylene group, however, it is not limited to them. Furthermore, the alkylene group may be unsubstituted or substituted with a $C_1$-$C_{20}$ alkyl group, a $C_2$-$C_{20}$ alkenyl group, or a $C_6$-$C_{20}$ aryl group.

In the metallocene compound according to the present invention, it is preferable that A in Chemical Formula 1 is hydrogen, methyl group, ethyl group, propyl group, isopropyl group, n-butyl group, tert-butyl group, methoxymethyl group, tert-butoxybutyl group, 1-ethoxyethyl group, 1-methyl-1-methoxyethyl group, tetrahydropyranyl group, or tetrahydrofuranyl group, however, it is not limited to them.

In the metallocene compound according to the present invention, B in Chemical Formula 1 is preferably silicon, however, it is not limited to this.

Because the metallocene compound of Chemical Formula 1 includes the structure in which an indenoindole derivative and an fluorene derivative are asymmetrically crosslinked by a bridge and has an unshared electron pair which can act as a Lewis base in the ligand structure, it can show high polymerization activity even when it is supported on the surface of a carrier having a Lewis acid character. Furthermore, it is superior in activity because of including electron-rich indenoindole group and low in hydrogen reactivity because of a proper steric hindrance and an electronic effect of the ligand, and thus it maintains high activity even in the presence of hydrogen. Furthermore, it can be used for preparing an olefinic polymer of ultra high molecular weight because nitrogen atom of the indenoindole derivative stabilizes the beta-hydrogen of growing polymer chain with a hydrogen bond and inhibits beta-hydrogen elimination.

According to one embodiment of the present invention, specific example of the structure represented by Chemical Formula 2a may be represented by the following structural formulae, however, it is not limited to them:

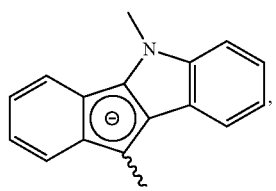

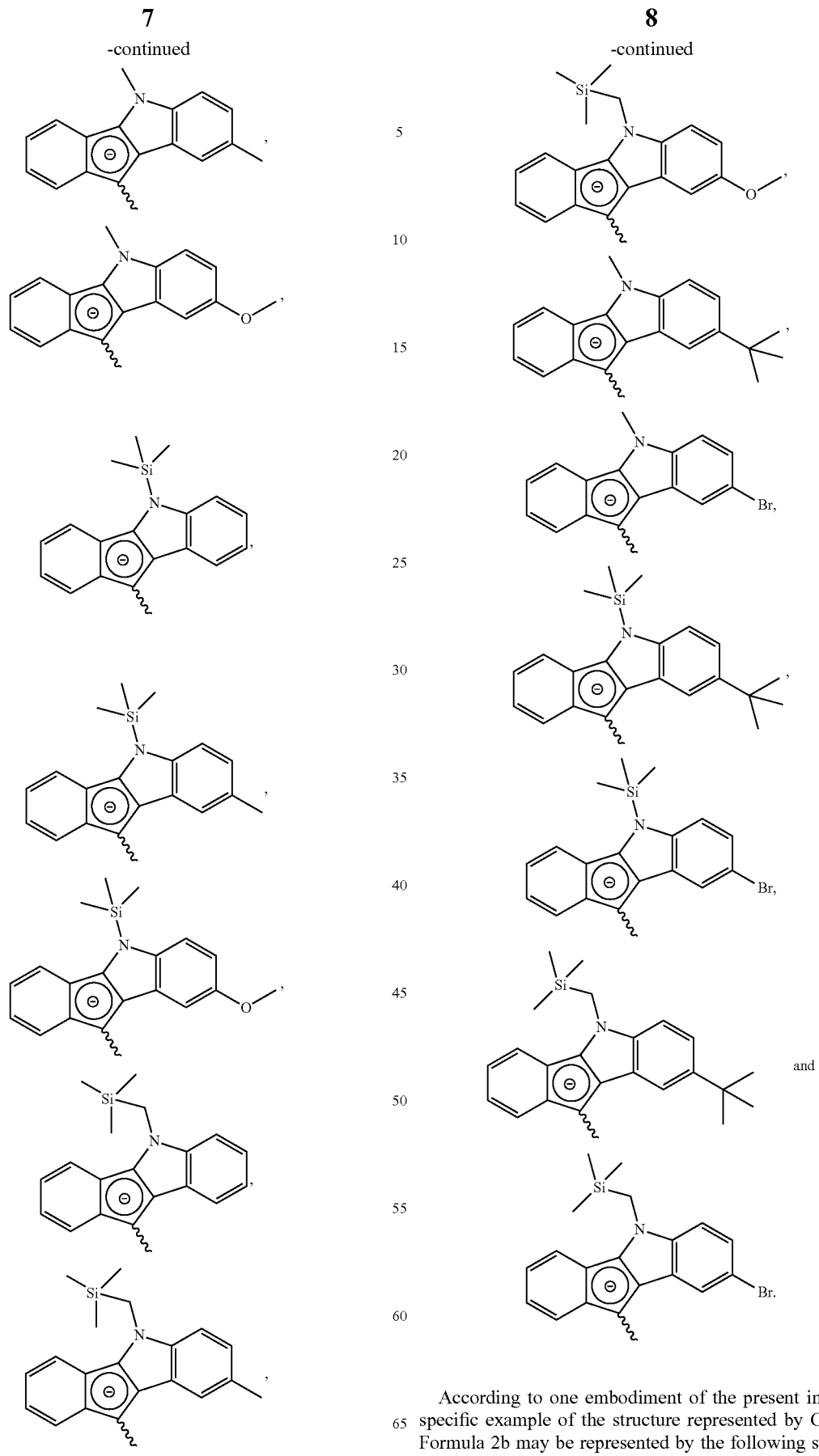
According to one embodiment of the present invention, specific example of the structure represented by Chemical Formula 2b may be represented by the following structural formulae, however, it is not limited to them:

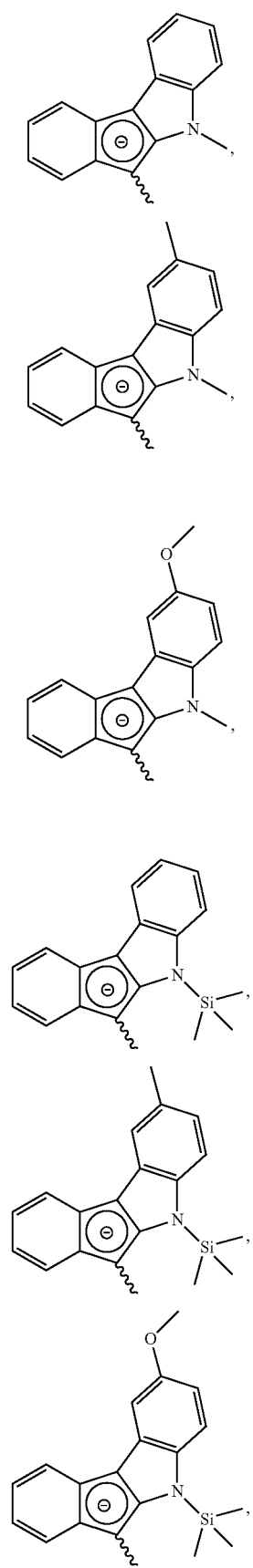
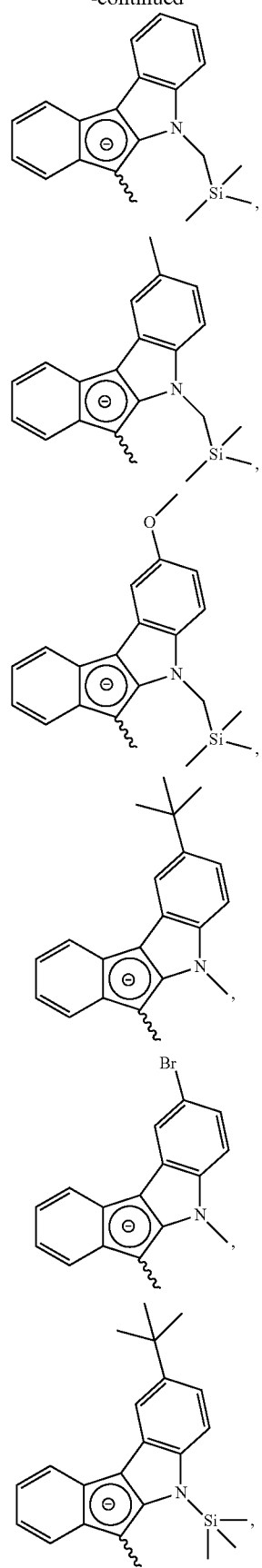

-continued

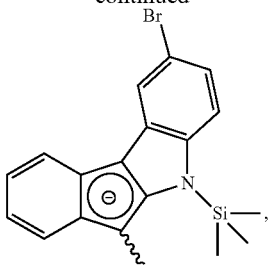

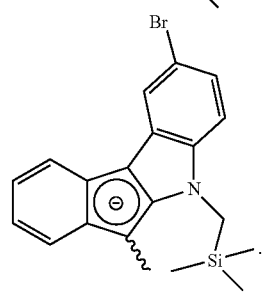

According to one embodiment of the present invention, specific example of the structure represented by Chemical Formula 3 may be represented by the following structural formulae, however, it is not limited to them:

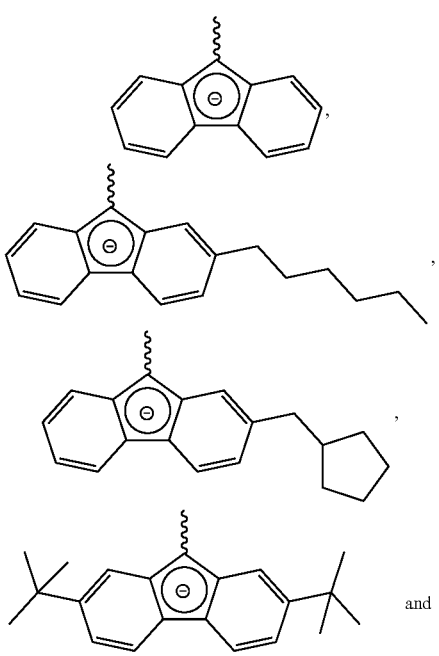

and

-continued

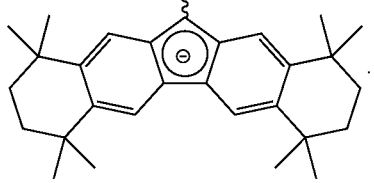

According to one embodiment of the present invention, specific example of the structure represented by Chemical Formula 1 may be represented by the following structural formulae, however, it is not limited to them:

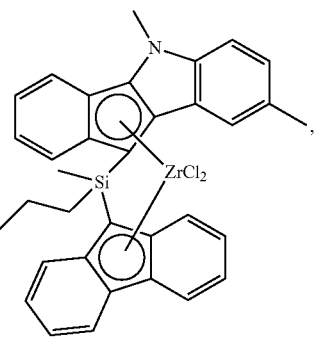

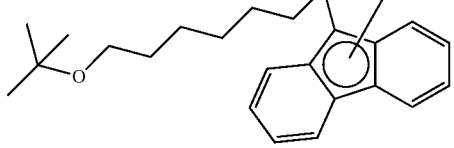

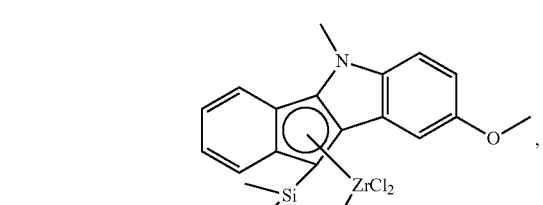

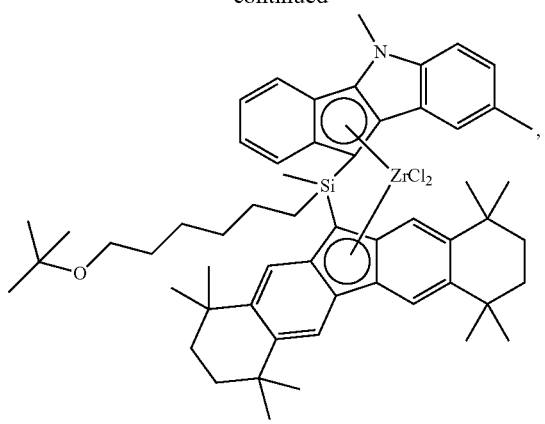
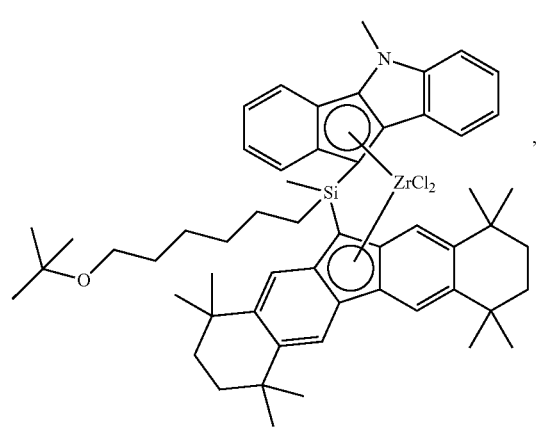
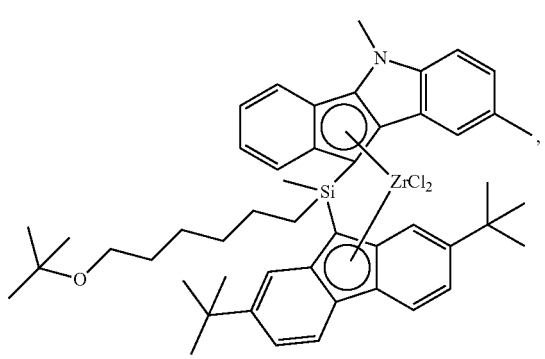
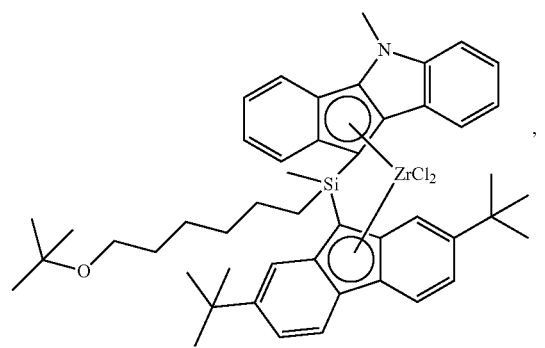
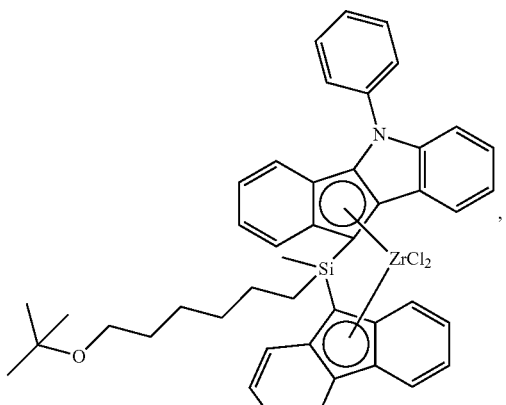
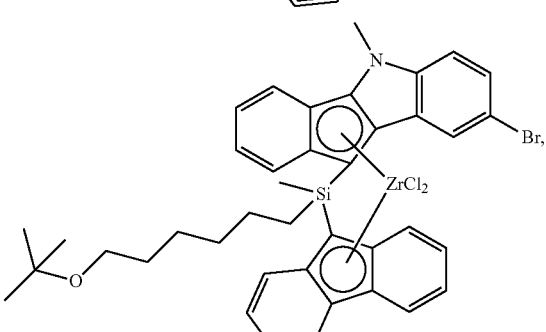
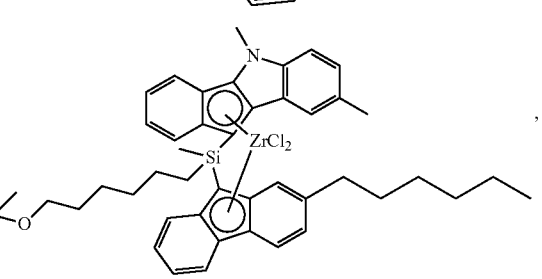
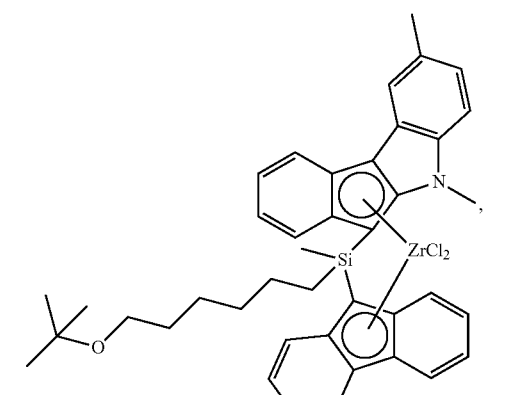
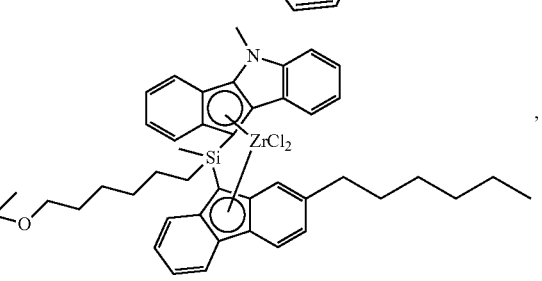

-continued

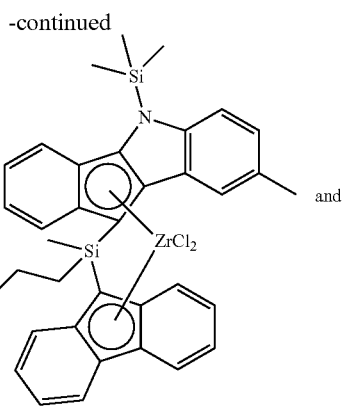

and

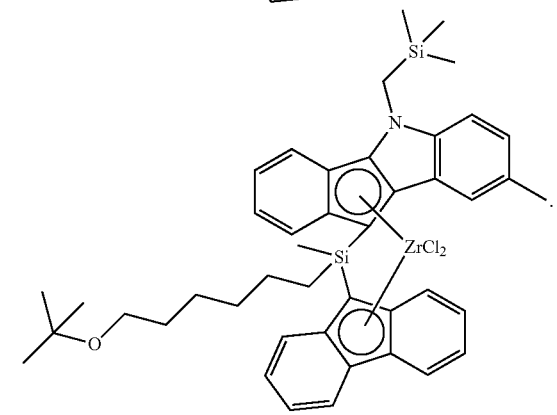

.

The metallocene compound according to the present invention is superior in activity and can polymerize an olefinic polymer having high molecular weight. Particularly, it can show high polymerization activity even when it is supported on a carrier. Therefore, it can prepare an olefinic polymer of ultra high molecular weight when it is used as a supported catalyst.

Furthermore, the metallocene compound according to the present invention can polymerize an olefinic polymer of ultra high molecular weight with still high activity because of its low hydrogen reactivity, even when the polymerization reaction is carried out in the presence of hydrogen in order to prepare an olefinic polymer having high molecular weight and wide molecular weight distribution at the same time. Therefore, the compound can prepare an olefinic polymer satisfying the high molecular characteristic without a decrease in activity even when it is heterogeneously used with a catalyst having different characteristic, and thus the olefinic polymer having high molecular weight and wide molecular weight distribution together can be easily prepared.

The metallocene compound of Chemical Formula 1 may be obtained by connecting an indenoindole derivative (C1) and a fluorene derivative (C2) with a bridge compound for preparing a ligand compound, and carrying out a metallation by putting a metal precursor compound therein, however, it is not limited to this.

More specifically, for example, after preparing a lithium salt by reacting an indenoindole derivative (C1) and a fluorene derivative (C2) with an organic lithium compound such as n-BuLi, the ligand compound is prepared by mixing a halogenated compound of a bridge compound therewith and reacting the mixture. After mixing the ligand compound or the lithium salt thereof and the metal precursor compound and reacting the same for about 12 to 24 hrs until the reaction is completed, the metallocene compound of Chemical Formula 1 may be obtained by filtering the reaction product and drying the same under a decompressed condition.

The preparation method of the metallocene compound according to the present invention is concretely disclosed in the following Examples.

The present invention also provides a catalyst composition including the metallocene compound and a cocatalyst.

The catalyst composition according to the present invention may further include at least one cocatalyst represented by Chemical Formula 4, Chemical Formula 5, or Chemical Formula 6:

$$-[Al(R18)-O]_n-$$ [Chemical Formula 4]

In Chemical Formula 4, each R18 may be same or different, and is independently a halogen; a $C_1$-$C_{20}$ hydrocarbon; or a halogen-substituted $C_1$-$C_{20}$ hydrocarbon; and n is an integer of 2 or more;

$$J(R18)_3$$ [Chemical Formula 5]

In Chemical Formula 5,

R18 is same as that in Chemical Formula 4; and

J is aluminum or boron;

$$[E-H]^+[ZA'_4]^- \text{ or } [E]^+[ZA'_4]^-$$ [Chemical Formula 6]

In Chemical Formula 6,

E is a neutral or cationic Lewis acid;

H is hydrogen atom;

Z is group 13 element; and each A' may be same or different, and is independently a $C_6$-$C_{20}$ aryl group or a $C_1$-$C_{20}$ alkyl group of which at least one hydrogen atom is unsubstituted or substituted with a halogen, a $C_1$-$C_{20}$ hydrocarbon, an alkoxy, or phenoxy.

Representative example of the compound of Chemical Formula 4 may be methylaluminoxane, ethylaluminoxane, isobutylaluminoxane, butylaluminoxane, and the like, and more preferable compound may be methylaluminoxane.

Representative example of the compound represented by Chemical Formula 5 may be trimethylaluminum, triethylaluminum, triisobutylaluminum, tripropylaluminum, tributylaluminum, dimethyl chloro aluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminum methoxide, dimethylaluminum ethoxide, trimethylboron, triethylboron, triisobutylboron, tripropylboron, tributylboron, and the like, and more preferable compound may be selected from trimethylaluminum, triethylaluminum, and triisobutylaluminum.

Representative example of the compound of Chemical Formula 6 may be triethylammonium tetraphenylboron, tributylammonium tetraphenylboron, trimethylammonium tetraphenylboron, tripropylammonium tetraphenylboron, trimethylammonium tetra(p-tolyl)boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetrapentafluorophenylboron, N,N-diethylanilinium tetraphenylboron, N,N-diethylanilinium tetrapentafluorophenylboron, diethylammonium tetrapentafluorophenylboron, triphenylphosphonium tetraphenylboron, trimethylphosphonium tetraphenylboron, triethylammonium tetraphenylaluminum, tributylammonium tetraphenylaluminum, trimethylammonium tetraphenylaluminum, tripropylammonium tetraphenylaluminum, trimethylammonium tetra(p-tolyl) aluminum, tripropylammonium tetra(p-tolyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetrapentafluorophenylaluminum, diethylammonium tetrapentatetraphenyl aluminum, triphenylphosphonium tetraphenylaluminum, trimethylphosphonium tetraphenylaluminum, tripropylammonium tetra(p-tolyl)boron, triethylammonium tetra(o,p-dimethylphenyl)boron, tributylammonium tetra(p-trifluoromethylphenyl)boron, triphenylcarbonium tetra(p-trifluoromethylphenyl)boron, triphenylcarbonium tetrapentafluorophenylboron, and the like.

Alumoxane may be used preferably, and methylalumoxane (MAO), an alkyl alumoxane, may be used more preferably.

The catalyst composition according to the present invention may be prepared by the method including the steps of 1) contacting the metallocene compound represented by Chemical Formula 1 with the compound represented by Chemical Formula 4 or Chemical Formula 5 and obtaining a mixture; and 2) adding the compound represented by Chemical Formula 6 into the mixture, as the first method.

Furthermore, the catalyst composition according to the present invention may be prepared by the method of contacting the metallocene compound represented by Chemical Formula 1 with the compound represented by Chemical Formula 4, as the second method.

In the first method of preparing the catalyst composition, the mole ratio of the metallocene compound represented by Chemical Formula 1/the compound represented by Chemical Formula 4 or Chemical Formula 5 is preferably 1/5,000 to 1/2, more preferably 1/1,000 to 1/10, and still more preferably 1/500 to 1/20. When the mole ratio of the metallocene compound represented by Chemical Formula 1/the compound represented by Chemical Formula 4 or Chemical Formula 5 is larger than 1/2, there is a problem of that the alkylating agent is very small in quantity and the metal compound is not completely alkylated, and when the mole ratio is lesser than 1/5,000, the alkylation of the metal compound is accomplished but there is a problem of that the alkylated metal compound is not completely activated due to the side reaction between the remaining excess alkylating agent and the activator of Chemical Formula 6. Furthermore, the mole ratio of the metallocene compound represented by Chemical Formula 1/the compound represented by Chemical Formula 6 is preferably 1/25 to 1, more preferably 1/10 to 1, and still more preferably 1/5 to 1. When the mole ratio of the metallocene compound represented by Chemical Formula 1/the compound represented by Chemical Formula 6 is larger than 1, there is a problem of that the activity of the prepared catalyst composition is deteriorated because the activator is relatively small in quantity and the metal compound is not completely activated, and when the mole ratio is lesser than 1/25, the activation of the metal compound is completely accomplished but there is a problem of that the cost of the catalyst composition is not economical or the purity of the polymer prepared by using the same is decreased due to the remaining excess activator.

In the second method of preparing the catalyst composition, the mole ratio of the metallocene compound represented by Chemical Formula 1/the compound represented by Chemical Formula 4 is preferably 1/10,000 to 1/10, more preferably 1/5,000 to 1/100, and still more preferably 1/3,000 to 1/500. When the mole ratio is larger than 1/10, there is a problem of that the activity of the prepared catalyst composition is deteriorated because the activator is relatively small in quantity and the metal compound is not completely activated, and when the mole ratio is lesser than 1/10,000, the activation of the metal compound is completely accomplished but there is a problem of that the cost of the catalyst composition is not economical or the purity of the polymer prepared by using the same is decreased due to the remaining excess activator.

As the reaction solvent for preparing the catalyst composition, a hydrocarbon solvent such as pentane, hexane, heptane, and the like, or an aromatic solvent such as benzene, toluene, and the like may be used.

Furthermore, the catalyst composition may include the metallocene compound and the cocatalyst in the form of that they are supported on a carrier.

When the metallocene compound and the cocatalyst are used in the form of being supported on a carrier, the amount of the metallocene compound may be about 0.5 to about 20 parts by weight and the amount of the cocatalyst may be about 1 to about 1,000 parts by weight, per 100 parts by weight of the carrier. Preferably, the amount of the metallocene compound may be about 1 to about 15 parts by weight and the amount of the cocatalyst may be about 10 to about 500 parts by weight, per 100 parts by weight of the carrier. And, more preferably, the amount of the metallocene compound may be about 1 to about 100 parts by weight and the amount of the cocatalyst may be about 40 to about 150 parts by weight, per 100 parts by weight of the carrier.

Meanwhile, the carrier may be a metal, a metal salt, or a metal oxide that is usually used as a carrier of a supported catalyst, and it is not limited. Specifically, it may include any carrier selected from the group consisting of silica, silica-alumina and silica-magnesia. The carrier may be dried at high temperature, and generally it may include an oxide, a carbonate, a sulfate or a nitrate of a metal, such as $Na_2O$, $K_2CO_3$, $BaSO_4$, $Mg(NO_3)_2$, and so on.

The less hydroxy (—OH) groups on the surface of the carrier, the better, but it is practically difficult to eliminate all of hydroxy groups. The amount of hydroxy groups may be controlled by the preparation method, the preparation conditions, the drying conditions (temperature, time, drying method, and so on), and so on of the carrier, and it is preferably 0.1 to 10 mmol/g, more preferably 0.1 to 1 mmol/g, and still more preferably 0.1 to 0.5 mmol/g. In order to reduce the side-reaction by some hydroxy groups left after drying, a carrier from which hydroxy groups are chemically eliminated with preserving siloxane groups having large reactivity for supporting may be used.

The present invention also provides a method of preparing an olefinic polymer including the step of polymerizing olefinic monomers in the presence of the catalyst composition including the metallocene compound, and an olefinic polymer prepared by the preparation method.

The polymerization reaction may be carried out according to a solution polymerization process, slurry process, or a gas phase process by using a continuous slurry polymerization reactor, a loop slurry reactor, a gas phase reactor, or a solution reactor. Furthermore, the reaction may be a homopolymerization of an olefinic monomer or copolymerization of two or more monomers.

The polymerization of the olefinic monomer may be carried out at the temperature of about 25 to about 500° C. and the pressure of about 1 to about 100 kgf/cm² for about 1 to about 24 hrs. Specifically, the polymerization of the olefinic monomer may be carried out at the temperature of about 25 to about 200° C., and preferably about 50 to about 100° C. Furthermore, the reaction pressure may be about 1 to about 100 kgf/cm², preferably about 1 to about 50 kgf/cm², and more preferably about 5 to about 40 kgf/cm².

In the olefinic polymer prepared according to the present invention, specific example of the olefinic monomer may be ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene, and the like, it is also possible to copolymerize two or more monomers among them by mixture.

The olefinic polymer may be polyethylene polymer but it is not limited to this.

In the case of that the olefinic polymer is the ethylene/α-olefin copolymer, the content of α-olefin, a comonomer, is not limited particularly, and it may be adequately selected according to the use or purpose of the olefinic polymer. More specifically, it may be over 0 mole % and 99 mole % or less.

The olefinic polymer prepared by the method can show high molecular weight.

According to one embodiment of the present invention, the weight average molecular weight (Mw) of the olefinic polymer may be about 50,000 to about 3,000,000 g/mol, or about 70,000 to about 2,000,000 g/mol. Particularly, when the olefinic polymer is prepared by using a catalyst composition including the metallocene compound supported on a carrier, it is possible to prepare the olefinic polymer having high molecular weight of about 500,000 g/mol or more, for example, about 500,000 to about 3,000,000 g/mol, or about 500,000 to about 2,000,000 g/mol.

Furthermore, the molecular weight distribution (Mw/Mn) of the olefinic polymer may be about 1.5 to about 20, and preferably about 2.0 to about 10.

Furthermore, according to one embodiment of the present invention, the density of the olefinic polymer may be about 0.85 to about 0.96 g/cm³, and preferably about 0.90 to about 0.95 g/cm³.

Therefore, the olefinic polymer according to the present invention shows ultra high molecular weight and can be variously applied according to its use.

Hereinafter, the present invention provides preferable examples for illuminating the present invention. However, following examples are only for understanding the present invention, and the range of the present invention is not limited to or by them.

EXAMPLES

Preparation Examples of Metallocene Compounds

Preparation Example 1

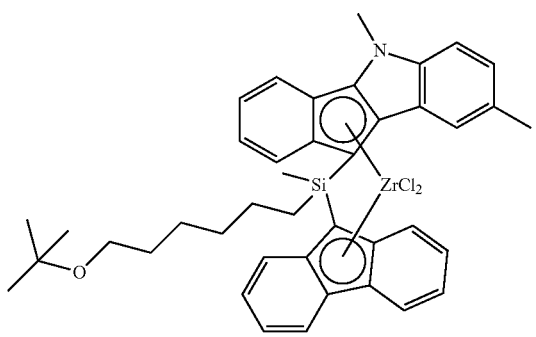

1-1 Preparation of Ligand Compound

After dissolving 2 g of fluorene in 5 mL of MTBE and 100 mL of hexane, 5.5 mL of 2.5 M n-BuLi hexane solution was added thereto in drops in a dry ice/acetone bath and the mixture was stirred overnight at room temperature. 3.6 g of (6-(tert-butoxy)hexyl)dichloro(methyl)silane was dissolved in 50 mL of hexane, and the fluorene-Li slurry was transferred thereto for 30 mins in a dry ice/acetone bath and the mixture was stirred overnight at room temperature. At the same time, 5,8-dimethyl-5,10-dihydroindeno[1,2-b]indole (12 mmol, 2.8 g) was also dissolved in 60 mL of THF, 5.5 mL of 2.5M n-BuLi hexane solution was added thereto in drops in a dry ice/acetone bath, and the mixture was stirred overnight at room temperature. After sampling the product and checking the completion of the reaction of fluorene and (6-(tert-butoxy)hexyl)dichloro(methyl)silane in the reaction solution through NMR analysis, 5,8-dimethyl-5,10-dihydroindeno[1,2-b]indole-Li solution was transferred thereto in a dry ice/acetone bath and the mixture was stirred overnight at room temperature. After the reaction, the reacted product was extracted with ether/water, the remaining moisture in the organic layer was eliminated with MgSO₄, and then ligand compound (Mw 597.90, 12 mmol) was obtained. Here, it was recognized by 1H-NMR analysis that two isomers were formed.

¹H NMR (500 MHz, d6-benzene): −0.30~−0.18 (3H, d), 0.40 (2H, m), 0.65~1.45 (8H, m), 1.12 (9H, d), 2.36~2.40 (3H, d), 3.17 (2H, m), 3.41~3.43 (3H, d), 4.17~4.21 (1H, d), 4.34~4.38 (1H, d), 6.90~7.80 (15H, m)

1-2 Preparation of Metallocene Compound

After dissolving 7.2 g (12 mmol) of the ligand compound synthesized in process 1-1 in 50 mL of diethyl ether, 11.5 mL of 2.5 M n-BuLi hexane solution was added thereto in drops in a dry ice/acetone bath and the mixture was stirred overnight at room temperature. Sticky oil of brown color was obtained by vacuum drying the same and slurry was obtained by dissolving the sticky oil in toluene. ZrCl₄(THF)₂ was prepared in the form of slurry by adding 50 mL of toluene thereto. 50 mL of ZrCl₄(THF)₂/toluene slurry was transferred to the sticky oil slurry in a dry ice/acetone bath. The slurry mixture was stirred overnight at room temperature and it was changed into violet color. The reacted solution was filtered for eliminating LiCl. After vacuum drying the filtrate for eliminating toluene therefrom, hexane was added thereto and the mixture was sonicated for 1 hr. After filtering the slurry, 6 g (Mw 758.02, 7.92 mmol, yield 66 mol %) of filtered solid metallocene compound of dark violet color was obtained. It was recognized by 1H-NMR analysis that two isomers were formed.

¹H NMR (500 MHz, CDCl₃): 1.19 (9H, d), 1.71 (3H, d), 1.50~1.70 (4H, m), 1.79 (2H, m), 1.98~2.19 (4H, m), 2.58 (3H, s), 3.38 (2H, m), 3.91 (3H, d), 6.66~7.88 (15H, m)

Preparation Example 2

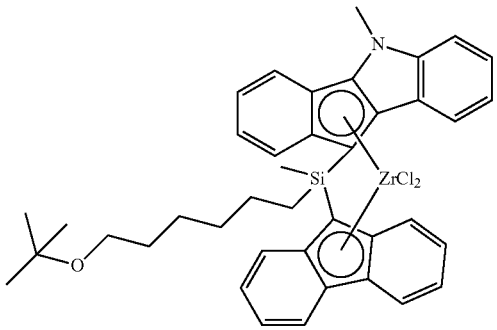

2-1 Preparation of Ligand Compound

After putting 1.7 g (10 mmol) of fluorene in a dried 250 mL Schlenk flask, 50 mL of MTBE was added thereto. After cooling the MTBE solution to −78° C., the inside of the flask was replaced by argon and 4.8 mL (12 mmol) of 2.5 M n-BuLi hexane solution was slowly added thereto in drops. After heating the reaction mixture slowly to room temperature, the mixture was stirred overnight. After putting 2.7 g (10 mmol) of (6-(tert-butoxy)hexyl)dichloro(methyl)silane in another 250 mL Schlenk flask under an argon atmosphere, 50 mL of hexane was added thereto and the mixture was stirred. After cooling the flask to −78° C., the lithiated solution of fluorene was very slowly added thereto in drops through a cannula. After the addition of the lithiated solution was completed, the mixture was slowly heated to room temperature and reacted overnight. After the reaction, a small dose of the product was collected under an argon atmosphere and vacuum dried, and the synthesis of (6-(tert-butoxy)hexyl)chloro(9H-fluoren-9-yl)(methyl)silane was recognized by NMR analysis.

$^1$H NMR (500 MHz, $C_6D_6$): −0.01 (3H, s), 1.12 (9H, m), 1.03~1.46 (10H, m), 3.17 (2H, t), 3.87 (1H, s), 7.15~7.78 (8H, m)

2.2 g (10 mmol) of 5-methyl-5,10-dihydroindeno[1,2-b]indole was put in a dried 250 mL Schlenk flask and dissolved in 40 mL of THF. Subsequently, 4.8 mL (12 mmol) of 2.5 M n-BuLi hexane solution was slowly added thereto in drops at −78° C. and the mixture was stirred for a day. The lithiated solution of 5-methyl-5,10-dihydroindeno[1,2-b]indole was slowly added to previously synthesized (6-(tert-butoxy)hexyl)chloro(9H-fluoren-9-yl)(methyl)silane solution in drops at −78° C. After overnight reaction, the product was extracted with ether/water and the oily ligand compound was obtained by eliminating the remaining moisture from the organic layer with $MgSO_4$ and vacuum drying the same.

$^1$H NMR (500 MHz, $CDCl_3$): −0.242 (3H, d), 1.12 (9H, s), 0.35~1.42 (10H, m), 3.2 (2H, m), 3.42 (3H, d), 4.18 (1H, d), 4.33 (1H, d), 6.99~7.92 (16H, m)

2-2 Preparation of Metallocene Compound

After putting 5.6 g (9.52 mmol) of the ligand compound synthesized in process 2-1 in a dried 250 mL Schlenk flask and dissolving the same in 50 mL of toluene and adding 2 mL (10 mmol) of MTBE thereto, 8 mL (20 mmol) of 2.5 M n-BuLi hexane solution was added thereto in drops in a dry ice/acetone bath and the mixture was stirred overnight at room temperature. Slurry (suspension) was prepared by putting 3.8 g (10 mmol) of $ZrCl_4(THF)_2$ in a 250 mL Schlenk flask under an argon atmosphere and adding toluene thereto. After cooling above two flasks to −78° C., the lithiated ligand compound was slowly added to the $ZrCl_4$ $(THF)_2$/toluene slurry. After the addition was completed, the reaction mixture was slowly heated to room temperature and reacted for a day. After the reaction, the product was filtered under an argon atmosphere for eliminating LiCl and the obtained filtrate was vacuum dried. Subsequently, 100 mL of hexane was added thereto and the metallocene compound (78% yield) was obtained by stirring and filtering the same under an argon atmosphere.

$^1$H NMR (500 MHz, $CDCl_3$): 1.17 (9H, s), 1.71 (3H, d), 0.84~2.15 (10H, m), 3.35 (2H, m), 3.92 (3H, s), 6.65~8.08 (16H, m)

Preparation Example 3

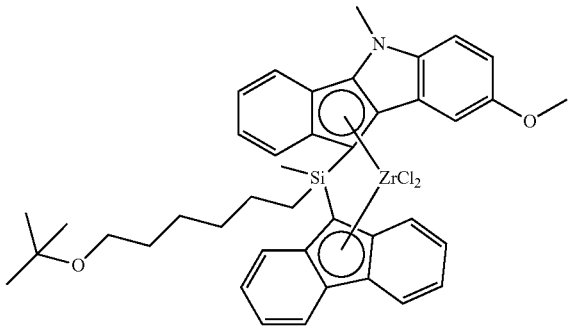

3-1 Preparation of Ligand Compound 1 g (6 mmol) of fluorene was put in a dried 250 mL Schlenk flask and 50 mL of THF was added thereto. After cooling the THF solution to −78° C. and replacing the inside of the flask with argon, 2.4 mL (6 mmol) of 2.5 M n-BuLi hexane solution was slowly added thereto in drops. After heating the reaction mixture slowly to room temperature, the mixture was stirred overnight. After putting 1.628 g (6 mmol) of (6-(tert-butoxy)hexyl)dichloro(methyl)silane in another 250 mL Schlenk flask under an argon atmosphere, 50 mL of hexane was added thereto and the mixture was stirred. After cooling the flask to −78° C., the lithiated solution of fluorene was very slowly added thereto in drops through a cannula. After the addition of the lithiated solution was completed, the mixture was slowly heated to room temperature and reacted overnight. After the reaction, a small dose of the product was collected under an argon atmosphere and vacuum dried, and the completion of the reaction was recognized by NMR analysis.

$^1$H NMR (500 MHz, $C_6D_6$): −0.01 (3H, s), 1.12 (9H, m), 1.03~1.46 (10H, m), 3.17 (2H, t), 3.87 (1H, s), 7.15~7.78 (8H, m)

1.5 g (6 mmol) of 8-methoxy-5-methyl-5,10-dihydroindeno[1,2-b]indole was put in a dried 250 mL Schlenk flask and dissolved in 40 mL of THF. Subsequently, 2.4 mL (6 mmol) of 2.5 M n-BuLi hexane solution was slowly added thereto in drops at −78° C. and the mixture was stirred for a day. The lithiated solution of 8-methoxy-5-methyl-5,10-dihydroindeno[1,2-b]indole was slowly added to previously synthesized (6-(tert-butoxy)hexyl)chloro(9H-fluoren-9-yl)(methyl)silane solution in drops at −78° C. After overnight reaction at room temperature, the product was extracted with ether/water and the oily ligand compound was obtained by eliminating the remaining moisture from the organic layer with $MgSO_4$ and vacuum drying the same.

$^1$H NMR (500 MHz, CDCl$_3$): −0.37 (3H, s), 0.21~1.5 (10H, m), 1.16 (9H, s), 3.29 (2H, t), 3.87 (3H, s), 4.01 (3H, s), 4.04 (1H, s), 4.09 (1H, s), 7.06~7.85 (15H, m)

3-2 Preparation of Metallocene Compound

After putting 3.3 g (5.4 mmol) of the ligand compound synthesized in process 3-1 in a dried 250 mL Schlenk flask and dissolving the same in 30 mL of toluene and adding 2 mL (10 mmol) of MTBE thereto, 5.2 mL (13 mmol) of 2.5 M n-BuLi hexane solution was added thereto in drops in a dry ice/acetone bath and the mixture was stirred overnight at room temperature. Slurry was prepared by putting 2.07 g (5.5 mmol) of ZrCl$_4$(THF)$_2$ in a 250 mL Schlenk flask under an argon atmosphere and adding toluene thereto. After cooling above two flasks to −78° C., the lithiated ligand compound was slowly added to the ZrCl$_4$(THF)$_2$/toluene slurry. After the addition was completed, the reaction mixture was slowly heated to room temperature and reacted for a day. After the reaction, the product was filtered under an argon atmosphere for eliminating LiCl and the obtained filtrate was vacuum dried. Subsequently, 100 mL of hexane was added thereto and the metallocene compound (yield 42%) was obtained by stirring and filtering the same under an argon atmosphere.

$^1$H NMR (500 MHz, CDCl$_3$): 1.16 (18H, m), 1.68 (3H, m), 0.85~2.14 (10H, m), 3.35 (2H, t), 3.88 (3H, d), 3.98 (3H, d), 6.72~7.82 (15H, m)

Preparation Example 4

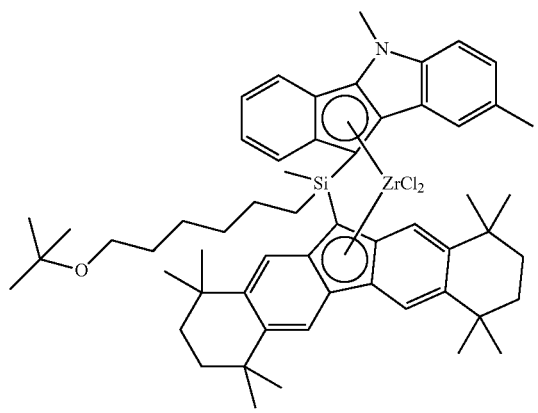

4-1 Preparation of Ligand Compound

After dissolving 3.9 g (10 mmol) of 1,1,4,4,7,7,10,10-octamethyl-2,3,4,7,8,9,10,12-octahydro-1H-dibenzo[b,h]fluorene (hereinafter, "OcOc Flu") in 3.6 mL (40 mmol) of MTBE and 77 mL of hexane, 6.4 mL of 2.5 M n-BuLi hexane solution was added thereto in drops in a dry ice/acetone bath and the mixture was stirred overnight at room temperature. 2.7 g (10 mmol) of (6-(tert-butoxy)hexyl)dichloro(methyl)silane was dissolved in 33 mL of hexane, and the OcOc Flu-Li slurry was transferred thereto for 30 mins in a dry ice/acetone bath and the mixture was stirred overnight at room temperature.

At the same time, 2.3 g (10 mmol) of 5,8-dimethyl-5,10-dihydroindeno[1,2-b]indole was also dissolved in 50 mL of THF, 8.0 mL of 2.5M n-BuLi hexane solution was added thereto in drops in a dry ice/acetone bath, and the mixture was stirred overnight at room temperature. 5,8-dimethyl-5,10-dihydroindeno[1,2-b]indole-Li solution was transferred to previously synthesized (6-(tert-butoxy)hexyl)chloro (12H-OcOc Flu-12-yl)(methyl)silane solution in a dry ice/acetone bath. After overnight reaction at room temperature, the product was extracted with ether/water and the oily ligand compound was obtained by eliminating the remaining moisture from the organic layer with MgSO$_4$ and vacuum drying the same.

NMR (500 MHz, d-Benzene): −0.00, −0.05 (3H, d), 1.14 (12H, s), 1.31~1.47 (12H, m), 1.63 (8H, m), 2.48 (3H, m), 3.22 (2H, m), 3.27 (3H, s), 3.67 (1H, s), 4.16 (1H, d), 7.29~7.52 (10H, m), 7.97 (1H, m).

4-2 Preparation of Metallocene Compound

The metallocene compound was prepared according to the same method as in process 3-2, except that 8.3 g (10.1 mmol) of the ligand compound synthesized in process 4-1 was used, 3.6 mL of MTBE and 80 mL of toluene were used as the solvent, and the experimental scale was regulated based on this. As the result, 7.4 g (yield 76.1%) of solid metallocene compound of dark violet color was obtained.

$^1$NMR (500 MHz, CDCl$_3$): 0.07 (3H, d), 1.16 (9H, m), 1.25 (4H, m), 1.28 (4H, m), 1.31~1.40 (24H, m), 1.44~1.71 (6H, m), 2.21 (2H, m), 2.19 (2H, m), 2.53 (3H, s), 3.36 (2H, m), 3.90 (3H, s), 6.72 (1H, m), 7.11~7.24 (2H, m), 7.32 (2H, d), 7.72 (5H, m), 7.96 (1H, d).

Preparation Example 5

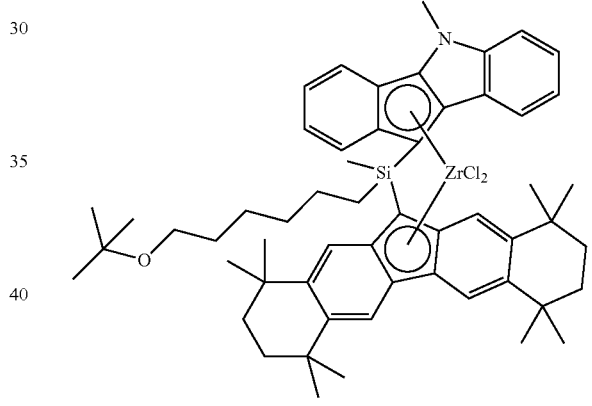

5-1 Preparation of Ligand Compound

The reaction was carried out according to the same method as in process 4-1, except that the experimental scale was regulated based on 1.95 g (5 mmol) of 1,1,4,4,7,7,10,10-octamethyl-2,3,4,7,8,9,10,12-octahydro-1H-dibenzo[b,h]fluorene, and 1.1 g (5 mmol) of 5-methyl-5,10-dihydroindeno[1,2-b]indole was used instead of 5,8-dimethyl-5,10-dihydroindeno[1,2-b]indole. As the result, 4.1 g of the black oily ligand compound was obtained.

NMR (500 MHz, d-Benzene): 0.38 (2H, m), 0.51 (2H, m), 0.75 (2H, m), 0.95 (2H, d), 1.12 (2H, m), 1.14 (9H, s), 1.24 (3H, m), 1.33~1.42 (24H, m), 3.26 (3H, s), 3.56 (2H, s), 3.58 (1H, s), 4.62 (1H, s), 7.11 (2H, d), 7.19~7.34 (8H, m), 7.68 (1H, m), 7.86 (1H, s), 7.93 (1H, s), 8.16 (1H, s).

5-2 Preparation of Metallocene Compound

The metallocene compound was prepared according to the same method as in process 3-2, except that 4.1 g (5 mmol) of the ligand compound synthesized in process 5-1 was used, 2.5 mL of MTBE and 50 mL of toluene were used as the solvent, and the experimental scale was regulated based on this. As the result, 2.1 g (yield 41.9%) of solid metallocene compound of dark violet color was obtained.

¹NMR (500 MHz, CDCl₃): 0.01 (9H, m), 0.88 (3H, m), 1.19~1.47 (32H, m), 1.72 (2H, m), 1.86 (2H, m), 3.90 (3H, s), 4.04 (2H, s), 6.18 (1H, s), 7.13~7.26 (4H, m), 7.40 (3H, m), 7.53 (2H, d), 7.74~7.76 (2H, m)

Preparation Example 6

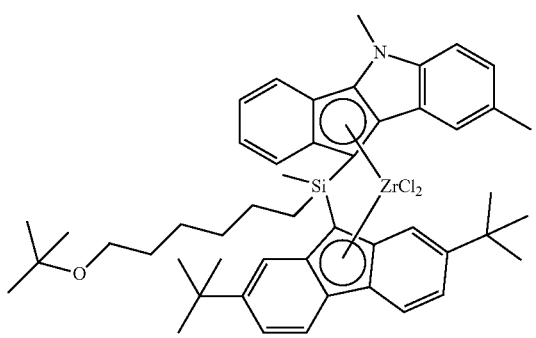

6-1 Preparation of Ligand Compound

After dissolving 2.8 g (10 mmol) of 2,7-di-tert-butyl-9H-fluorene in 4.8 mL of MTBE and 90 mL of hexane, 6.4 mL of 2.5M n-BuLi hexane solution was added thereto in drops in a dry ice/acetone bath and the mixture was stirred overnight at room temperature. 2.7 g (10 mmol) of (6-(tert-butoxy)hexyl)dichloro(methyl)silane was dissolved in 50 mL of hexane under an argon atmosphere, and the 2,7-di-tert-butyl-9H-fluorene-Li slurry was transferred thereto for 30 mins in a dry ice/acetone bath and the mixture was stirred overnight at room temperature. At the same time, 2.3 g (10 mmol) of 5,8-dimethyl-5-methyl-5,10-dihydroindeno[1,2-b]indole was also dissolved in 50 mL of THF, 8.0 mL (20 mmol) of 2.5M n-BuLi hexane solution was added thereto in drops in a dry ice/acetone bath, and the mixture was stirred overnight at room temperature. After checking the completion of the reaction of 2,7-di-tert-butyl-9H-fluorene and (6-(tert-butoxy)hexyl)dichloro(methyl)silane in the reaction solution through NMR analysis, the 5,8-dimethyl-5-methyl-5,10-dihydroindeno [1,2-b]indole-Li solution was transferred thereto in a dry ice/acetone bath and the mixture was stirred overnight at room temperature. After the reaction, the reacted product was extracted with ether/water and 7.3 g (10 mmol) of ligand compound was obtained by eliminating the remaining moisture from the organic layer with MgSO₄ and vacuum drying the same.

NMR (500 MHz, d-Benzene): -0.03, -0.04 (3H, d), 0.46~0.90 (6H, m), 1.06 (2H, m), 1.13 (9H,$), 1.28~1.33 (18H, m), 1.62 (2H, m), 2.49 (3H, s), 3.22 (2H, m), 3.35, 3.54 (1H, d), 3.75 (1H, d), 4.15 (1H, d), 7.02 (1H, d), 7.10 (2H, m), 7.19~7.49 (8H, m), 7.71 (1H, m), 7.78~7.86 (2H, m).

6-2 Preparation of Metallocene Compound

The metallocene compound was prepared according to the same method as in process 3-2, except that 7.3 g (10 mmol) of the ligand compound synthesized in process 6-1 was used, 3.6 mL of MTBE and 80 mL of toluene were used as the solvent, and the experimental scale was regulated based on this. As the result, 2.4 g (yield 28.0%) of solid metallocene compound of dark violet color was obtained.

¹NMR (500 MHz, CDCl₃): 0.96 (9H, s), 1.17 (9H, s), 1.28~1.62 (4H, m), 1.66 (3H, s), 1.82 (2H, m), 2.08 (2H, m), 2.23 (2H, m), 2.49 (3H, s), 3.35 (2H, t), 3.88 (3H, s), 6.73 (1H, t), 7.12 (3H, s), 7.25 (1H, d), 7.46 (2H, m), 7.61~7.68 (3H, m), 7.74 (1H, s), 7.84 (2H, m).

Preparation Example 7

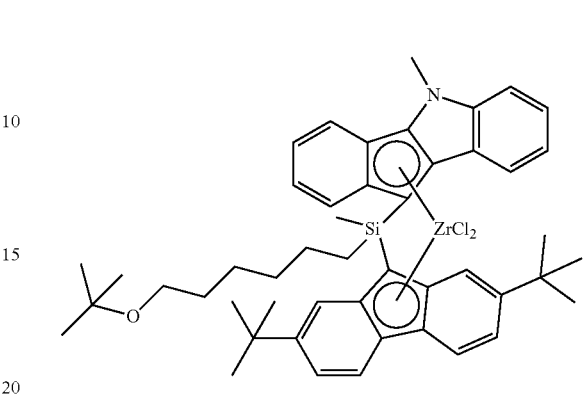

7-1 Preparation of Ligand Compound

The reaction was carried out according to the same method as in process 6-1, except that the experimental scale was regulated based on 1.4 g (5 mmol) of 2,7-di-tert-butyl-9H-fluorene, and 1.1 g (5 mmol) of 5-methyl-5,10-dihydroindeno[1,2-b]indole was used instead of 5,8-dimethyl-5,10-dihydroindeno[1,2-b]indole. As the result, 3.4 g (4.8 mmol) of the black oily ligand compound was obtained.

NMR (500 MHz, d-Benzene): -0.06, -0.04 (3H, d), 0.52~1.08 (10H, m), 1.13 (18H, m), 1.38 (9H, m), 3.89, 3.97 (1H, d), 4.06 (1H, d), 7.21~7.95 (13H, m).

7-2 Preparation of Metallocene Compound

The metallocene compound was prepared according to the same method as in process 3-2, except that 3.4 g (4.8 mmol) of the ligand compound synthesized in process 7-1 was used, 2.3 mL of MTBE and 50 mL of toluene were used as the solvent, and the experimental scale was regulated based on this. As the result, 2.2 g (yield 42.8%) of solid metallocene compound of dark violet color was obtained.

¹NMR (500 MHz, CDCl₃): 0.97 (9H, s), 1.17 (9H, s), 1.27 (9H, s), 1.54 (2H, m), 1.62 (2H, m), 1.72 (3H, s), 1.81 (2H, m), 2.13 (2H, m), 2.21 (2H, m), 3.36 (2H, t), 3.91 (3H, s), 6.73 (1H, t), 7.13 (3H, m), 7.38~7.51 (3H, m), 7.63~7.74 (5H, m), 8.10 (1H, d).

Preparation Example 8

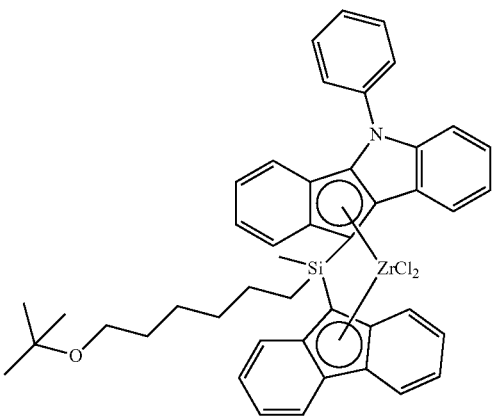

8-1 Preparation of Ligand Compound 1 g (6 mmol) of fluorene was put in a dried 250 mL Schlenk flask and 50 mL of THF was added thereto. After cooling the THF solution to −78° C. and replacing the inside of the flask with argon, 2.9 mL (7.2 mmol) of 2.5 M nBuLi hexane solution was added thereto in drops in a dry ice/acetone bath and the mixture was stirred overnight at room temperature. After putting 1.63 g (6 mmol) of (6-(tert-butoxy)hexyl)dichloro(methyl)silane in another 250 mL Schlenk flask under an argon atmosphere, 50 mL of hexane was added thereto and the mixture was stirred. After cooling the flask to −78° C., the lithiated solution of fluorene was very slowly added thereto in drops through a cannula. After the addition of the lithiated solution was completed, the mixture was slowly heated to room temperature and reacted overnight. After the reaction, a small dose of the product was collected under an argon atmosphere and vacuum dried, and the completion of the reaction was recognized by NMR analysis.

$^1$H NMR (500 MHz, C$_6$D$_6$): −0.01 (3H, s), 1.12 (9H, m), 1.03~1.46 (10H, m), 3.17 (2H, t), 3.87 (1H, s), 7.15~7.78 (8H, m)

1.7 g (6 mmol) of 5-phenyl-5,10-dihydroindeno[1,2-b]indole was put in a dried 250 mL Schlenk flask and dissolved in 40 mL of THF. Subsequently, 2.9 mL (7.2 mmol) of 2.5 M n-BuLi hexane solution was slowly added thereto in drops at −78° C. and the mixture was stirred for a day at room temperature. The lithiated solution of 5-phenyl-5,10-dihydroindeno[1,2-b]indole was slowly added to previously synthesized (6-(tert-butoxy)hexyl)chloro(9H-fluoren-9-yl)(methyl)silane solution in drops at −78° C. After overnight reaction at room temperature, the product was extracted with ether/water and the ligand compound was obtained by eliminating the remaining moisture from the organic layer with MgSO$_4$ and vacuum drying the same.

$^1$H NMR (500 MHz, CDCl$_3$): −0.45 (3H, d), 0.86 (9H, s), 0.80~1.2 (10H, m), 2.95 (2H, m), 3.45 (1H, s), 3.76 (1H, s), 6.71~7.52 (16H, m)

8-2 Preparation of Metallocene Compound

After putting 3.47 g (5.37 mmol) of the ligand compound synthesized in process 8-1 in a dried 250 mL Schlenk flask and dissolving the same in 50 mL of toluene and adding, 2 mL (10 mmol) of MTBE thereto, 5.2 mL (13 mmol) of 2.5 M n-BuLi hexane solution was added thereto in drops in a dry ice/acetone bath and the mixture was stirred overnight at room temperature. Slurry was prepared by putting 2.02 g (5.4 mmol) of ZrCl$_4$(THF)$_2$ in a 250 mL Schlenk flask under an argon atmosphere and adding toluene thereto. After cooling above two flasks to −78° C., the lithiated ligand compound was slowly added to the ZrCl$_4$(THF)$_2$/toluene slurry. After the addition was completed, the reaction mixture was slowly heated to room temperature and reacted for a day. After the reaction, the product was filtered under an argon atmosphere for eliminating LiCl and the obtained filtrate was vacuum dried. Subsequently, 100 mL of hexane was added thereto and the metallocene compound (yield 53.2%) was obtained by stirring and filtering the same under an argon atmosphere.

$^1$H NMR (500 MHz, CDCl$_3$): 1.16 (9H, s), 1.62 (3H, s), 1.17~2.14 (10H, m), 3.35 (2H, m), 6.96~7.83 (21H, m)

Preparation Example 9

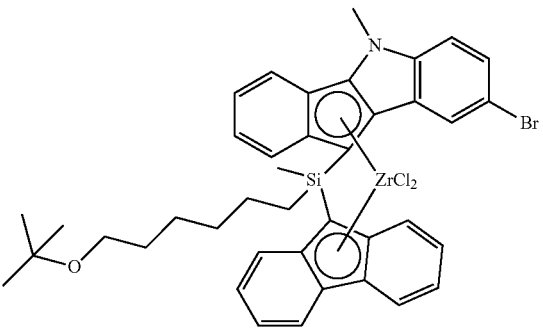

9-1 Preparation of Ligand Compound 1 g (6 mmol) of fluorene was put in a dried 250 mL Schlenk flask and 50 mL of THF was added thereto. After cooling the THF solution to −78° C., 2.9 mL (7.2 mmol) of 2.5 M n-BuLi hexane solution was slowly added thereto in drops. After heating the reaction mixture slowly to room temperature, the mixture was stirred overnight. After putting 1.63 g (6 mmol) of (6-(tert-butoxy)hexyl)dichloro(methyl)silane in another 250 mL Schlenk flask under an argon atmosphere, 50 mL of hexane was added thereto and the mixture was stirred. After cooling the flask to −78° C., the lithiated solution of fluorene was very slowly added thereto in drops through a cannula. After the addition of the lithiated solution was completed, the mixture was slowly heated to room temperature and reacted overnight. After the reaction, a small dose of the product was collected under an argon atmosphere and vacuum dried, and the completion of the reaction was recognized by NMR analysis.

$^1$H NMR (500 MHz, C$_6$D$_6$): −0.01 (3H, s), 1.12 (9H, m), 1.03~1.46 (10H, m), 3.17 (2H, t), 3.87 (1H, s), 7.15~7.78 (8H, m)

1.7 g (6 mmol) of 8-bromo-5-methyl-5,10-dihydroindeno[1,2-b]indole was put in a dried 250 mL Schlenk flask and dissolved in 40 mL of THF. Subsequently, 2.9 mL (7.2 mmol) of 2.5 M n-BuLi hexane solution was slowly added thereto in drops at −78° C. and the mixture was stirred for a day. The lithiated solution of 8-bromo-5-methyl-5,10-dihydroindeno[1,2-b]indole was slowly added to previously synthesized (6-(tert-butoxy)hexyl)chloro(9H-fluoren-9-yl)(methyl)silane solution in drops at −78° C. After overnight reaction at room temperature, the product was extracted with ether/water and the ligand compound was obtained by eliminating the remaining moisture from the organic layer with MgSO$_4$ and vacuum drying the same.

$^1$H NMR (500 MHz, CDCl$_3$): −0.37 (3H, s), 1.32 (9H, s), 0.56~1.51 (10H, m), 3.32 (2H, m), 4.03 (3H, s), 3.98 (1H, s), 4.01 (1H, s), 7.1~7.86 (15H, m)

9-2 Preparation of Metallocene Compound

After putting 3.82 g (5.76 mmol) of the ligand compound synthesized in process 9-1 in a dried 250 mL Schlenk flask and dissolving the same in 50 mL of toluene and adding 2 mL (10 mmol) of MTBE thereto, 5.5 mL (13.8 mmol) of 2.5 M n-BuLi hexane solution was added thereto in drops in a dry ice/acetone bath and the mixture was stirred overnight at room temperature. Slurry was prepared by putting 2.17 g (5.76 mmol) of ZrCl$_4$(THF)$_2$ in a 250 mL Schlenk flask under an argon atmosphere and adding toluene thereto. After cooling above two flasks to −78° C., the lithiated ligand compound was slowly added to the ZrCl$_4$(THF)$_2$/toluene slurry. After the addition was completed, the reaction mixture was slowly heated to room temperature and reacted for a day. After the reaction, the product was filtered under an argon atmosphere for eliminating LiCl and the obtained filtrate was vacuum dried. Subsequently, 100 mL of hexane was added thereto and the metallocene compound (yield 49.5%) was obtained by stirring and filtering the same under an argon atmosphere.

$^1$H NMR (500 MHz, CDCl$_3$): 1.17 (9H, s), 1.68 (3H, s), 0.82~2.16 (10H, m), 3.36 (2H, m), 3.96 (3H, s), 7.02~7.83 (15H, m)

Preparation Example 10

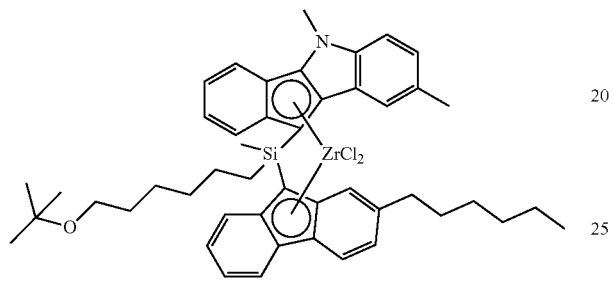

10-1 Preparation of Ligand Compound 1.16 g (5 mmol) of 5,8-dimethyl-5,10-dihydroindeno[1,2-b]indole was put in a dried 250 mL Schlenk flask and 50 mL of THF was added thereto. After cooling the THF solution to −78° C., 2.4 mL (6 mmol) of 2.5 M n-BuLi hexane solution was slowly added thereto in drops. After heating the reaction mixture slowly to room temperature, the mixture was stirred overnight. After putting 1.35 g (5 mmol) of (6-(tert-butoxy)hexyl)dichloro(methyl)silane in another 250 mL Schlenk flask under an argon atmosphere, 50 mL of hexane was added thereto and the mixture was stirred. After cooling the flask to −78° C., the lithiated solution of 5,8-dimethyl-5,10-dihydroindeno[1,2-b]indole was very slowly added thereto in drops through a cannula. After the addition of the lithiated solution was completed, the mixture was slowly heated to room temperature and reacted overnight.

1.25 g (5 mmol) of 2-hexyl-9H-fluorene was put in a dried 250 mL Schlenk flask and dissolved in 40 mL of THF. Subsequently, 2.4 mL (6 mmol) of 2.5 M n-BuLi hexane solution was slowly added thereto in drops at −78° C. and the mixture was stirred for a day. The lithiated solution of 2-hexyl-9H-fluorene was slowly added to previously synthesized 10-((6-(tert-butoxy)hexyl)dichloro(methyl)silyl-5,8-dimethyl-5,10-dihydroindeno[1,2-b]indole solution in drops at −78° C. After overnight reaction at room temperature, the product was extracted with ether/water and the ligand compound was obtained by eliminating the remaining moisture from the organic layer with MgSO$_4$ and vacuum drying the same.

$^1$H NMR (500 MHz, C$_6$D$_6$): −0.15 (3H, s), 1.12 (9H, s), 0.82 (3H, t), 1.28 (6H, m), 1.59 (2H, m), 1.0~1.6 (10H, m), 2.3 (2H, t), 2.64 (2H, t), 2.4 (3H, s), 4.1 (3H, s), 7.1~7.82 (14H, m)

10-2 Preparation of Metallocene Compound

After putting 3.4 g (5 mmol) of the ligand compound synthesized in process 10-1 in a dried 250 mL Schlenk flask and dissolving the same in 50 mL of toluene and adding 2 mL (10 mmol) of MTBE thereto, 4.4 mL (11 mmol) of 2.5 M n-BuLi hexane solution was added thereto in drops in a dry ice/acetone bath and the mixture was stirred overnight at room temperature. Slurry was prepared by putting 1.88 g (5 mmol) of ZrCl$_4$(THF)$_2$ in a 250 mL Schlenk flask under an argon atmosphere and adding toluene thereto. After cooling above two flasks to −78° C., the lithiated ligand compound was slowly added to the ZrCl$_4$(THF)$_2$/toluene slurry. After the addition was completed, the reaction mixture was slowly heated to room temperature and reacted for a day. After the reaction, the product was filtered under an argon atmosphere for eliminating LiCl and the obtained filtrate was vacuum dried. Subsequently, 100 mL of hexane was added thereto and the metallocene compound (yield 52%) was obtained by stirring and filtering the same under an argon atmosphere.

$^1$H NMR (500 MHz, CDCl$_3$): 1.17 (9H, s), 1.68 (3H, s), 0.87 (3H, m), 1.19 (6H, m), 1.32 (2H, m), 2.48 (2H, m), 0.9~2.1 (10H, m), 2.5 (3H, s), 3.46 (2H, m), 3.9 (3H, s), 7.04~7.91 (14H, m)

Preparation Example 11

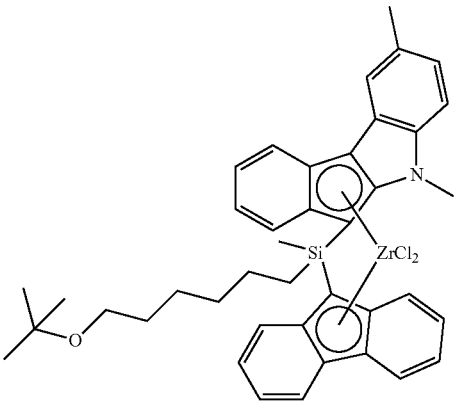

11-1 Preparation of Ligand Compound 1.1 g (5 mmol) of 5-methyl-5,6-dihydroindeno[1,2-b]indole was put in a dried 250 mL Schlenk flask and 50 mL of THF was added thereto. After cooling the THF solution to −78° C., 2.4 mL (6 mmol) of 2.5 M n-BuLi hexane solution was slowly added thereto in drops. After heating the reaction mixture slowly to room temperature, the mixture was stirred overnight. After putting 1.35 g (5 mmol) of (6-(tert-butoxy)hexyl)dichloro(methyl)silane in another 250 mL Schlenk flask under an argon atmosphere, 50 mL of hexane was added thereto and the mixture was stirred. After cooling the flask to −78° C., the lithiated solution of 5-methyl-5,6-dihydroindeno[1,2-b]indole was very slowly added thereto in drops through a cannula. After the addition of the lithiated solution was completed, the mixture was slowly heated to room temperature and reacted overnight.

0.83 g (5 mmol) of fluorene was put in a dried 250 mL Schlenk flask and dissolved in 40 mL of THF. Subsequently, 2.4 mL (6 mmol) of 2.5 M n-BuLi hexane solution was slowly added thereto in drops at −78° C. and the mixture was stirred for a day. The lithiated solution of fluorene was slowly added to previously synthesized 6-((6-(tert-butoxy)hexyl)dichloro(methyl)silyl-5-methyl-5,6-dihydroindeno[1,2-b]indole solution in drops at −78° C. After overnight reaction at room temperature, the product was extracted with ether/water and the ligand compound was obtained by eliminating the remaining moisture from the organic layer with MgSO$_4$ and vacuum drying the same.

$^1$H NMR (500 MHz, C$_6$D$_6$): −0.2 (3H, s), 1.2 (9H, s), 0.88 (3H, t), 1.28 (6H, m), 1.59 (2H, m), 0.8~1.5 (10H, m), 2.3 (2H, t), 2.64 (2H, t), 4.1 (3H, s), 7.1~7.82 (15H, m)

11-2 Preparation of Metallocene Compound

After putting 2.93 g (5 mmol) of the ligand compound synthesized in process 11-1 in a dried 250 mL Schlenk flask and dissolving the same in 50 mL of toluene and adding 2 mL (10 mmol) of MTBE thereto, 4.4 mL (11 mmol) of 2.5 M n-BuLi hexane solution was added thereto in drops in a dry ice/acetone bath and the mixture was stirred overnight at room temperature. Slurry was prepared by putting 1.88 g (5 mmol) of ZrCl$_4$(THF)$_2$ in a 250 mL Schlenk flask under an argon atmosphere and adding toluene thereto. After cooling above two flasks to −78° C., the lithiated ligand compound was slowly added to the ZrCl$_4$(THF)$_2$/toluene slurry. After the addition was completed, the reaction mixture was slowly heated to room temperature and reacted for a day. After the reaction, the product was filtered under an argon atmosphere for eliminating LiCl and the obtained filtrate was vacuum dried. Subsequently, 100 mL of hexane was added thereto and the metallocene compound (yield 68%) was obtained by stirring and filtering the same under an argon atmosphere.

$^1$H NMR (500 MHz, CDCl$_3$): 1.22 (9H, s), 1.71 (3H, s), 0.87 (3H, m), 1.19 (6H, m), 1.32 (2H, m), 2.48 (2H, m), 0.9~2.1 (10H, m), 3.46 (2H, m), 4.15 (3H, s), 7.04~7.91 (15H, m)

Preparation Example 12

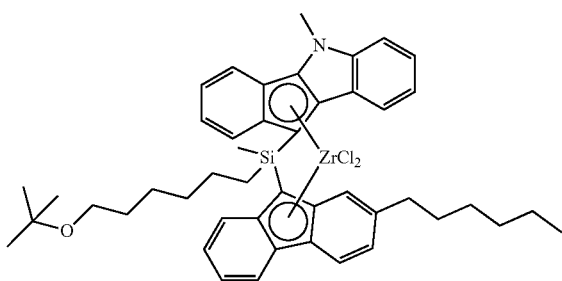

12-1 Preparation of Ligand Compound 1.1 g (5 mmol) of 5-methyl-5,10-dihydroindeno[1,2-b]indole was put in a dried 250 mL Schlenk flask and 50 mL of THF was added thereto. After cooling the THF solution to −78° C. and replacing the inside of the flask with argon, 2.4 mL (6 mmol) of 2.5 M n-BuLi hexane solution was slowly added thereto in drops. After heating the reaction mixture slowly to room temperature, the mixture was stirred overnight. After putting 1.35 g (5 mmol) of (6-(tert-butoxy)hexyl)dichloro(methyl)silane in another 250 mL Schlenk flask under an argon atmosphere, 50 mL of hexane was added thereto and the mixture was stirred. After cooling the flask to −78° C., the lithiated solution of 5-methyl-5,10-dihydroindeno[1,2-b]indole was very slowly added thereto in drops through a cannula. After the addition of the lithiated solution was completed, the mixture was slowly heated to room temperature and reacted overnight.

1.25 g (5 mmol) of 2-hexyl-9H-fluorene was put in a dried 250 mL Schlenk flask and dissolved in 40 mL of THF. Subsequently, 2.4 mL (6 mmol) of 2.5 M n-BuLi hexane solution was slowly added thereto in drops at −78° C. and the mixture was stirred for a day. The lithiated solution of 2-hexyl-9H-fluorene was slowly added to previously synthesized 10-(((6-(tert-butoxy)hexyl)dichloro(methyl)silyl)-5-methyl-5,10-dihydroindeno[1,2-b]indole solution in drops at −78° C. After overnight reaction at room temperature, the product was extracted with ether/water and the ligand compound was obtained by eliminating the remaining moisture from the organic layer with MgSO$_4$ and vacuum drying the same.

$^1$H NMR (500 MHz, C$_6$D$_6$): −0.2 (3H, s), 1.2 (9H, s), 0.88 (3H, t), 1.28 (6H, m), 1.59 (2H, m), 0.8~1.5 (10H, m), 2.3 (2H, t), 2.64 (2H, t), 4.1 (3H, s), 7.1~7.82 (15H, m)

12-2 Preparation of Metallocene Compound

After putting 3.34 g (5 mmol) of the ligand compound synthesized in process 12-1 in a dried 250 mL Schlenk flask and dissolving the same in 50 mL of toluene and adding 2 mL (10 mmol) of MTBE thereto, 4.4 mL (11 mmol) of 2.5 M n-BuLi hexane solution was added thereto in drops in a dry ice/acetone bath, and the mixture was stirred overnight at room temperature. Slurry was prepared by putting 1.88 g (5 mmol) of ZrCl$_4$(THF)$_2$ in a 250 mL Schlenk flask under an argon atmosphere and adding toluene thereto. After cooling above two flasks to −78° C., the lithiated ligand compound was slowly added to the ZrCl$_4$(THF)$_2$/toluene slurry. After the addition was completed, the reaction mixture was slowly heated to room temperature and reacted for a day. After the reaction, the product was filtered under an argon atmosphere for eliminating LiCl and the obtained filtrate was vacuum dried. Subsequently, 100 mL of hexane was added thereto and the metallocene compound (yield 68%) was obtained by stirring and filtering the same under an argon atmosphere.

$^1$H NMR (500 MHz, CDCl$_3$): 1.22 (9H, s), 1.71 (3H, s), 0.87 (3H, m), 1.19 (6H, m), 1.32 (2H, m), 2.48 (2H, m), 0.9~2.1 (10H, m), 3.46 (2H, m), 4.15 (3H, s), 7.04~7.91 (15H, m)

Preparation Examples of Supported Catalysts

Preparation Example 13

A silica carrier was prepared by dehydrating silica (SYLOPOL 948, produced by Grace Davison Co.) at 400° C. under a vacuum condition for 12 hrs.

After putting 100 mL of toluene solution in a glass reactor of room temperature and adding 10 g of the prepared silica carrier, the solution was stirred with elevating the temperature of the reactor to 40° C. When the silica was sufficiently dispersed, 60.6 mL of 10 wt % methylaluminoxane (MAO)/toluene solution was added thereto and the mixture was stirred with 200 rpm for 16 hrs after elevating the temperature to 80° C. Subsequently, the temperature thereof was decreased to 40° C. again and the unreacted aluminum compound was eliminated by washing the same with a sufficient amount of toluene. After putting 100 mL of toluene therein again, 0.5 mmol of the metallocene compound prepared in Preparation Example 1 was added thereto and the mixture was stirred for 2 hrs. After stopping stirring when the reaction was terminated, the toluene layer was separated and eliminated therefrom and the supported catalyst was obtained by decompressing the same at 40° C. for eliminating the remaining toluene.

Preparation Example 14

The supported catalyst was prepared according to the same method as in Preparation Example 13, except that 0.5 mmol of the metallocene compound prepared in Preparation Example 2 was used.

Comparative Preparation Example 1

The supported catalyst was prepared according to the same method as in Preparation Example 13, except that 0.5 mmol of (tert-Bu-O—(CH$_2$)$_6$)(CH$_3$)Si(C$_5$(CH$_3$)$_4$)(NCMe$_3$) TiCl$_2$ prepared according to Example 6 disclosed in Korean Patent No. 0690345 was used.

Comparative Preparation Example 2

The supported catalyst was prepared according to the same method as in Preparation Example 13, except that 0.5 mmol of (tert-Bu-O—(CH$_2$)$_6$)MeSi(9-C$_{13}$H$_9$)$_2$ZrCl$_2$ prepared according to Preparation Example 1 disclosed in Korean Patent No. 1154507 was used.

Examples of Solution Polymerization

Ethylene Polymerization

Example 1

A 300 mL Andrew bottle was assembled with impeller part and the inside thereof was replaced with argon in a glove box. After putting 180 mL of toluene in the Andrew bottle, 10 mL of MAO (10 wt % in toluene) solution was added thereto. 20 μmol of the metallocene compound catalyst prepared in Preparation Example 1 was put in a separate 100 mL flask and dissolved in 20 mL of toluene. 5 mL (5 μmol) of the catalyst solution was taken and put in the Andrew bottle, and the mixture was stirred for 5 mins. The Andrew bottle was immersed in an oil bath of 90° C. and the mixture was stirred for 5 mins by using a mechanical stirrer fixed at the upper part of the bottle until the temperature of the reaction solution reached 90° C. The inside of the bottle was purged with ethylene gas 3 times, and pressure was slowly raised up to 50 psig by opening the ethylene valve. The reaction was carried out for 30 mins with operating the mechanical stirrer with 500 rpm while maintaining the pressure by continuously providing ethylene as much as ethylene consumed. When the reaction finished, the gas in the reactor was slowly vented for reducing the pressure in the reactor after locking the ethylene valve and stopping stirring. After disassembling the cover of the reactor, the reacted product was poured in 400 mL of ethanol/aqueous HCl solution mixture, and the mixture was stirred for about 2 hrs and filtered. The polymer obtained by filtering was dried at 65° C. for 20 hrs in a vacuum oven. The obtained polymer was weighed for calculating the activity of the catalyst, and was used for additional analyses.

Examples 2 to 12

The ethylene polymerization was carried out according to the same method as in Example 1, except that the metallocene compound catalysts of Preparation Examples 2 to 12 were used respectively, and the obtained polymers were analyzed.

Ethylene-1-Hexene Copolymerization

Example 13

A 300 mL Andrew bottle was assembled with impeller part and the inside thereof was replaced with argon in a glove box. After putting 180 mL of toluene in the Andrew bottle, 10 mL of MAO (10 wt % in toluene) solution was added thereto. 20 μmol of the metallocene compound catalyst prepared in Preparation Example 1 was put in a separate 100 mL flask and dissolved in 20 mL of toluene. 5 mL (5 μmol) of the catalyst solution was taken and put in the Andrew bottle, and the mixture was stirred for 5 mins. The Andrew bottle was immersed in an oil bath of 90° C. and the mixture was stirred for 5 mins by using a mechanical stirrer fixed at the upper part of the bottle until the temperature of the reaction solution reached 90° C. After stopping stirring, 5 mL of 1-hexene was put in the bottle under an argon atmosphere, the inside of the bottle was purged with ethylene gas 3 times, and pressure was slowly raised up to 50 psig by opening the ethylene valve. The reaction was carried out for 30 mins with operating the mechanical stirrer with 500 rpm while maintaining the pressure by continuously providing ethylene as much as ethylene consumed. When the reaction finished, the gas in the reactor was slowly vented for reducing the pressure in the reactor after locking the ethylene valve and stopping stirring. After disassembling the cover of the reactor, the reacted product was poured in 400 mL of ethanol/aqueous HCl solution mixture, and the mixture was stirred for about 2 hrs and filtered. The polymer obtained by filtering was dried at 65° C. for 20 hrs in a vacuum oven. The obtained polymer was weighed for calculating the activity of the catalyst, and was used for additional analyses.

Examples 14 to 24

The ethylene-1-hexene copolymerization was carried out according to the same method as in Example 13, except that the metallocene compound catalysts of Preparation Examples 2 to 12 were used respectively, and the obtained polymers were analyzed.

The activities of the catalysts, and the molecular weights and distributions of the polymers of Examples 1 to 24 are listed in the following Table 1.

TABLE 1

|  | Catalysts Used | 1-Hx Input (unit: mL) | Activity (unit: kg/mmol/hr) | 1-Hexene Content (unit: mol %) | Mw (unit: g/mol) | Mw/Mn |
|---|---|---|---|---|---|---|
| Example 1 | Preparation Example 1 | 0 | 6.8 | — | 54,900 | 4.0 |
| Example 2 | Preparation Example 2 | 0 | 4.7 | — | 223,008 | 5.8 |
| Example 3 | Preparation Example 3 | 0 | 3.3 | — | 121,700 | 3.3 |
| Example 4 | Preparation Example 4 | 0 | 6.5 | — | 551,910 | 3.2 |

TABLE 1-continued

|  | Catalysts Used | 1-Hx Input (unit: mL) | Activity (unit: kg/mmol/hr) | 1-Hexene Content (unit: mol %) | Mw (unit: g/mol) | Mw/Mn |
|---|---|---|---|---|---|---|
| Example 5 | Preparation Example 5 | 0 | 1.9 | — | 274,030 | 7.6 |
| Example 6 | Preparation Example 6 | 0 | 4.2 | — | 193,380 | 6.9 |
| Example 7 | Preparation Example 7 | 0 | 4.6 | — | 468,470 | 5.0 |
| Example 8 | Preparation Example 8 | 0 | 4.7 | — | 161,400 | 6.9 |
| Example 9 | Preparation Example 9 | 0 | 4.4 | — | 178,800 | 5.4 |
| Example 10 | Preparation Example 10 | 0 | 4.9 | — | 209,920 | 9.7 |
| Example 11 | Preparation Example 11 | 0 | 4.0 | — | 173,500 | 3.9 |
| Example 12 | Preparation Example 12 | 0 | 5.6 | — | 129,000 | 5.3 |
| Example 13 | Preparation Example 1 | 5 | 7.6 | 6.7 | 91,200 | 2.4 |
| Example 14 | Preparation Example 2 | 5 | 3.3 | 5.1 | 197,832 | 3.3 |
| Example 15 | Preparation Example 3 | 5 | 3.6 | 4.7 | 169,000 | 2.9 |
| Example 16 | Preparation Example 4 | 5 | 7.3 | 4.9 | 316,430 | 3.7 |
| Example 17 | Preparation Example 5 | 5 | 2.0 | 2.1 | 186,620 | 5.3 |
| Example 18 | Preparation Example 6 | 5 | 3.1 | 6.5 | 195,070 | 6.1 |
| Example 19 | Preparation Example 7 | 5 | 4.4 | 5.4 | 185,160 | 3.8 |
| Example 20 | Preparation Example 8 | 5 | 4.4 | 4.0 | 127,200 | 16.5 |
| Example 21 | Preparation Example 9 | 5 | 4.0 | 6.1 | 162,500 | 2.9 |
| Example 22 | Preparation Example 10 | 5 | 3.8 | 5.6 | 200,610 | 5.7 |
| Example 23 | Preparation Example 11 | 5 | 4.7 | 3.9 | 129,700 | 3.5 |
| Example 24 | Preparation Example 12 | 5 | 3.5 | 5.5 | 195,000 | 5.6 |

Examples of Polymerization Using Supported Catalyst

Example 25

The catalyst was prepared by quantifying 30 mg of the supported catalyst prepared in Preparation Example 13 in a dry box, putting it in a 50 mL glass bottle, sealing the same with a rubber diaphragm, and taking the bottle out of the dry box. The polymerization was carried out in a temperature controlled 2 L metal alloy reactor which was equipped with a mechanical stirrer and could be used at high pressure.

After putting 1.2 L of hexane in which 1.0 mmol of triethylaluminum was included in the reactor and adding the supported catalyst prepared above to the reactor without contact with air, the polymerization was carried out at for 1 hr with continuously providing ethylene monomer gas at 80° C. with the pressure of 40 bar. The polymerization was terminated by stopping stirring, and venting and eliminating ethylene gas. The polymerization solvent was eliminated from the obtained polymer by filtering the same, and the polymer was dried at 80° C. for 12 hrs in a vacuum oven.

Example 26

The polymerization was carried out according to the same method as in Example 25, except that the supported catalyst prepared in Preparation Example 14 was used.

Comparative Example 1

The polymerization was carried out according to the same method as in Example 25, except that the supported catalyst prepared in Comparative Preparation Example 1 was used.

Comparative Example 2

The polymerization was carried out according to the same method as in Example 25, except that the supported catalyst prepared in Comparative Preparation Example 2 was used.

The activities of the catalysts, and the molecular weights and distributions of the polymers of Examples 25 to 26 and Comparative Examples 1 to 2 are listed in the following Table 2.

TABLE 2

|  | Catalysts Used | Activity (unit: kgPE/gCat/hr) | Mw (unit: g/mol) | Mw/Mn |
|---|---|---|---|---|
| Example 25 | Preparation Example 13 | 8.1 | 1,122,483 | 2.07 |
| Example 26 | Preparation Example 14 | 8.1 | 879,950 | 3.76 |
| Comparative Example 1 | Comparative Preparation Example 1 | 3.0 | 1,133,319 | 2.45 |
| Comparative Example 2 | Comparative Preparation Example 2 | 5.9 | 377,265 | 2.14 |

What is claimed is:

1. A metallocene compound represented by Chemical Formula 1:

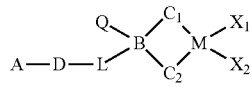

[Chemical Formula 1]

wherein in Chemical Formula 1:

A is hydrogen, a halogen, a $C_1$-$C_{20}$ alkyl group, a $C_2$-$C_{20}$ alkenyl group, a $C_6$-$C_{20}$ aryl group, a $C_7$-$C_{20}$ alkylaryl group, a $C_7$-$C_{20}$ arylalkyl group, a $C_1$-$C_{20}$ alkoxy group, a $C_2$-$C_{20}$ alkoxyalkyl group, a $C_3$-$C_{20}$ heterocycloalkyl group, or a $C_5$-$C_{20}$ heteroaryl group;

D is —O—, —S—, —N(R)—, or —Si(R)(R')—, wherein R and R' are, the same or different from each other, and are independently hydrogen, a halogen, a $C_1$-$C_{20}$ alkyl group, a $C_2$-$C_{20}$ alkenyl group, or a $C_6$-$C_{20}$ aryl group;

L is a $C_1$-$C_{10}$ linear or branched alkylene group;

B is carbon, silicon, or germanium;

Q is hydrogen, a halogen, a $C_1$-$C_{20}$ alkyl group, a $C_2$-$C_{20}$ alkenyl group, a $C_6$-$C_{20}$ aryl group, a $C_7$-$C_{20}$ alkylaryl group, or a $C_7$-$C_{20}$ arylalkyl group;

M is a group 4 transition metal;

$X_1$ and $X_2$ are the same or different from each other, and are independently hydrogen, a halogen, a $C_1$-$C_{20}$ alkyl group, a $C_2$-$C_{20}$ alkenyl group, a $C_6$-$C_{20}$ aryl group, a nitro group, an amido group, a $C_1$-$C_{20}$ alkylsilyl group, a $C_1$-$C_{20}$ alkoxy group, or a $C_1$-$C_{20}$ sulfonate group;

$C_1$ is represented by one of Chemical Formula 2a and Chemical Formula 2b:

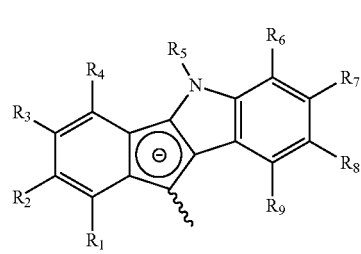

[Chemical Formula 2a]

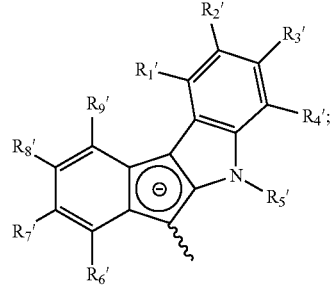

[Chemical Formula 2b]

and $C_2$ is represented by Chemical Formula 3:

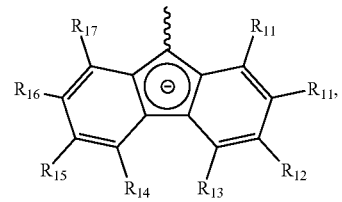

[Chemical Formula 3]

wherein in Chemical Formulae 2a, 2b and 3, $R_1$ to $R_{17}$ and $R_1'$ to $R_9'$ are the same or different from each other, and are independently hydrogen, a halogen, a $C_1$-$C_{20}$ alkyl group, a $C_2$-$C_{20}$ alkenyl group, a $C_1$-$C_{20}$ alkylsilyl group, a $C_1$-$C_{20}$ silylalkyl group, a $C_1$-$C_{20}$ alkoxysilyl group, a $C_1$-$C_{20}$ alkoxy group, a $C_6$-$C_{20}$ aryl group, a $C_7$-$C_{20}$ alkylaryl group, or a $C_7$-$C_{20}$ arylalkyl group, wherein 2 or more adjacent groups among $R_{10}$ to $R_{17}$ may form a substituted or unsubstituted aliphatic or aromatic ring by being connected together; and wherein B and M of Chemical Formula 1 are bonded to the cyclopentadienyl groups of $C_1$ and $C_2$ of Chemical Formula 1.

2. The metallocene compound according to claim 1, wherein $R_1$ to $R_{17}$ and $R_1'$ to $R_9'$ in Chemical Formulae 2a, 2b and 3 are independently hydrogen, a methyl group, an ethyl group, a propyl group, an isopropyl group, an n-butyl group, a tert-butyl group, a pentyl group, a hexyl group, a heptyl group, an octyl group, a phenyl group, a halogen group, a trimethylsilyl group, a triethylsilyl group, a tripropylsilyl group, a tributylsilyl group, a triisopropylsilyl group, a trimethylsilylmethyl group, a methoxy group, or an ethoxy group.

3. The metallocene compound according to claim 1, wherein L in Chemical Formula 1 is a $C_4$-$C_8$ linear or branched alkylene group.

4. The metallocene compound according to claim 1, wherein A in Chemical Formula 1 is hydrogen, a methyl group, an ethyl group, a propyl group, an isopropyl group, an n-butyl group, a tert-butyl group, a methoxymethyl group, a tert-butoxybutyl group, a 1-ethoxyethyl group, a 1-methyl-1-methoxyethyl group, a tetrahydropyranyl group, or a tetrahydrofuranyl group.

5. The metallocene compound according to claim 1, wherein the structure represented by Chemical Formula 2a is one of the following structures:

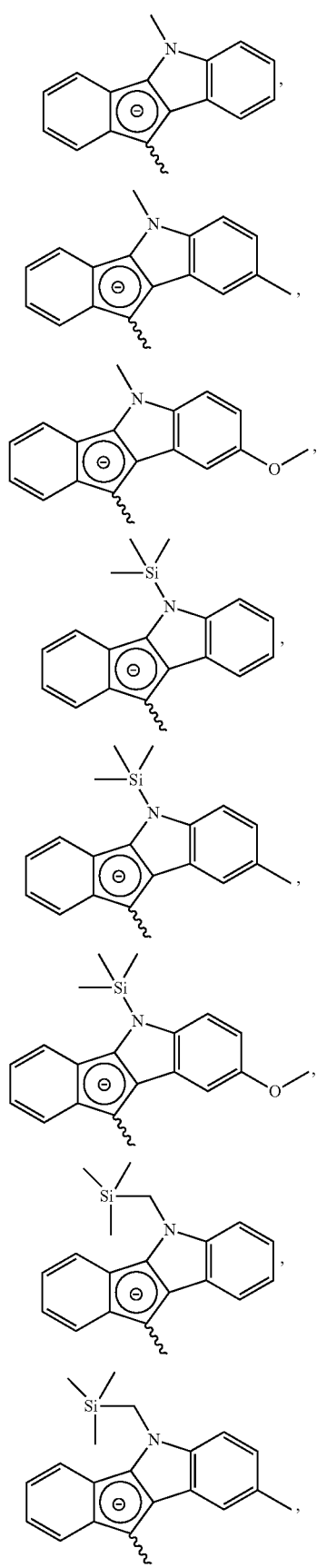
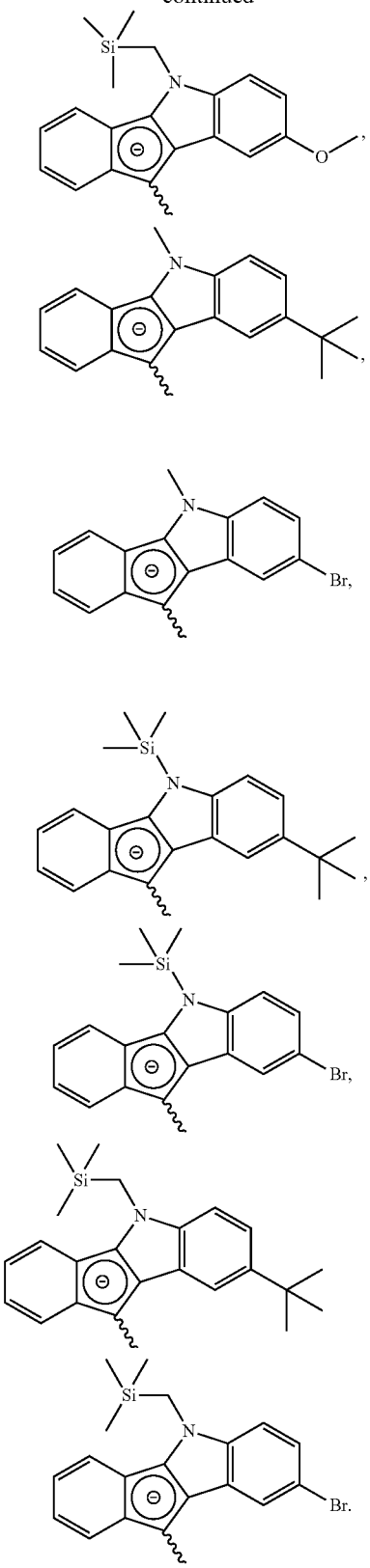
6. The metallocene compound according to claim 1, wherein the structure represented by Chemical Formula 2b is one of the following structures:

41
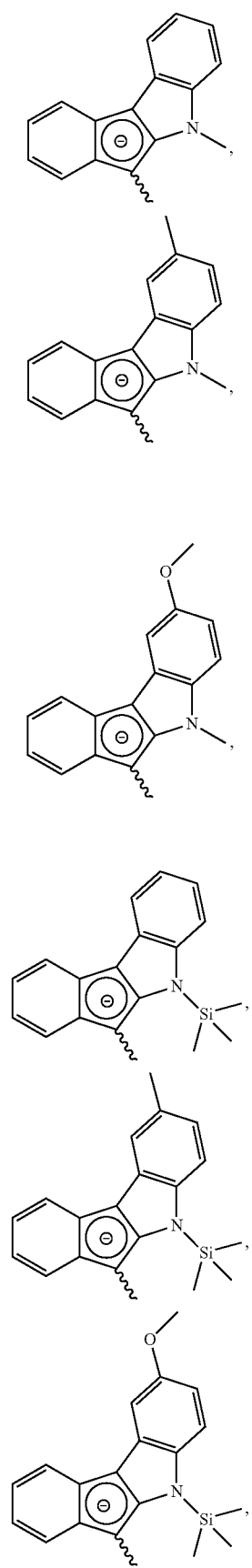
42
-continued
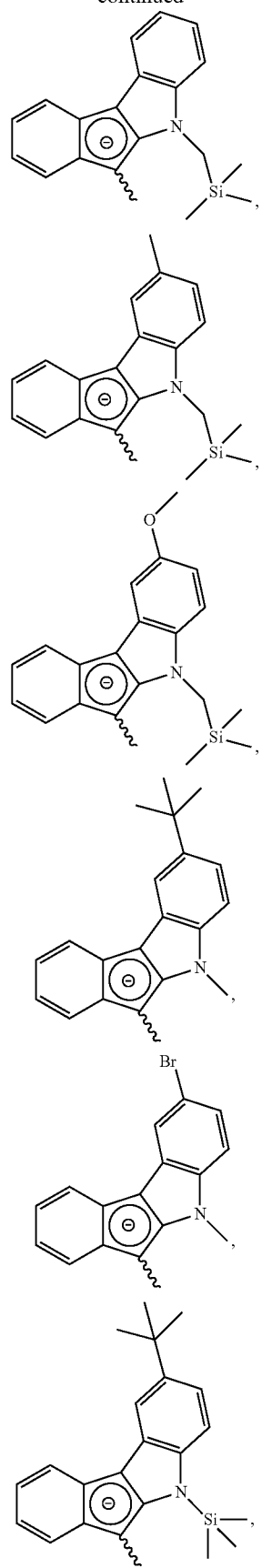

-continued
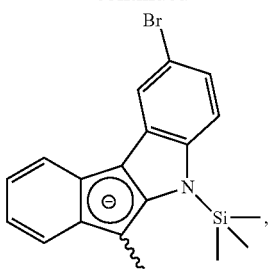
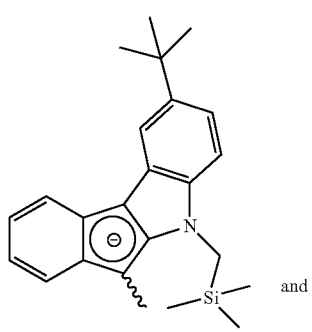 and
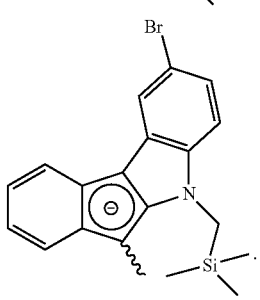
7. The metallocene compound according to claim 1, wherein the structure represented by Chemical Formula 3 is one of the following structures:
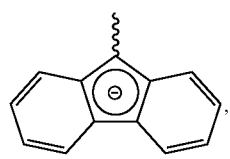,
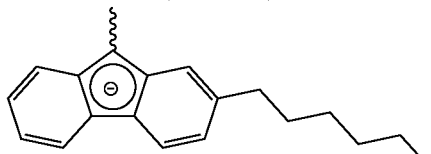,
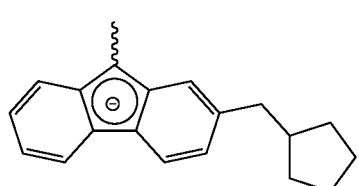,
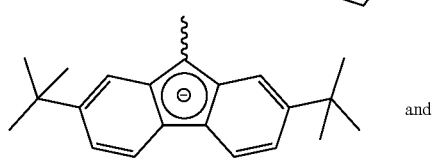 and
-continued
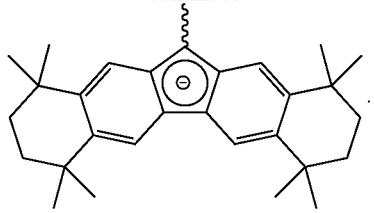
8. The metallocene compound according to claim 1, wherein the structure represented by Chemical Formula 1 is one of the following structures:
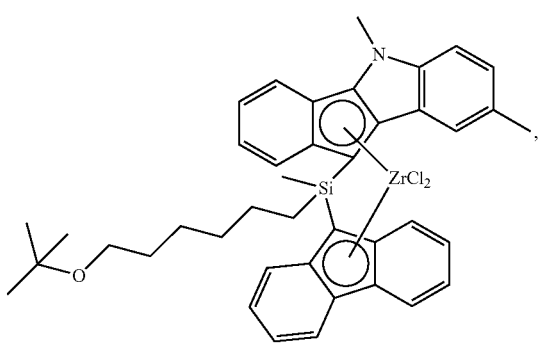,
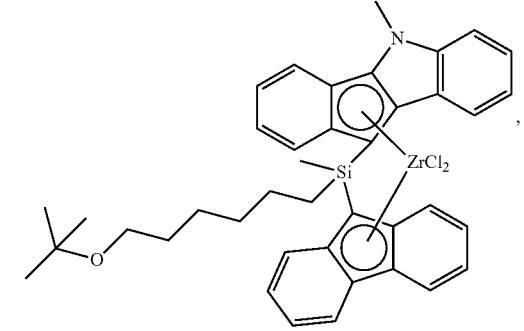,
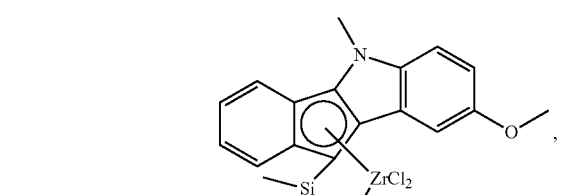,

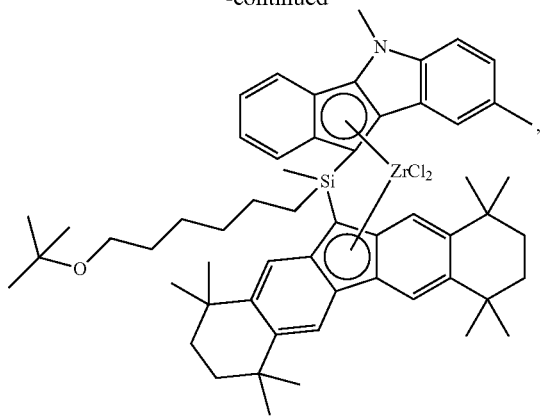
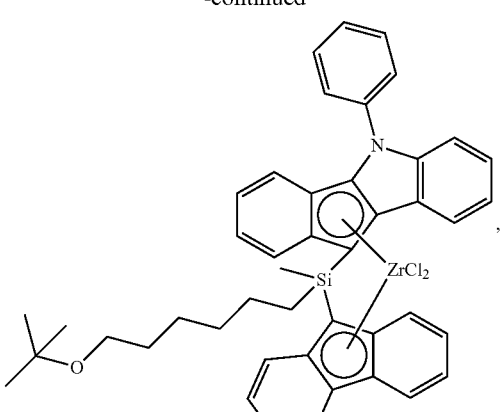

-continued

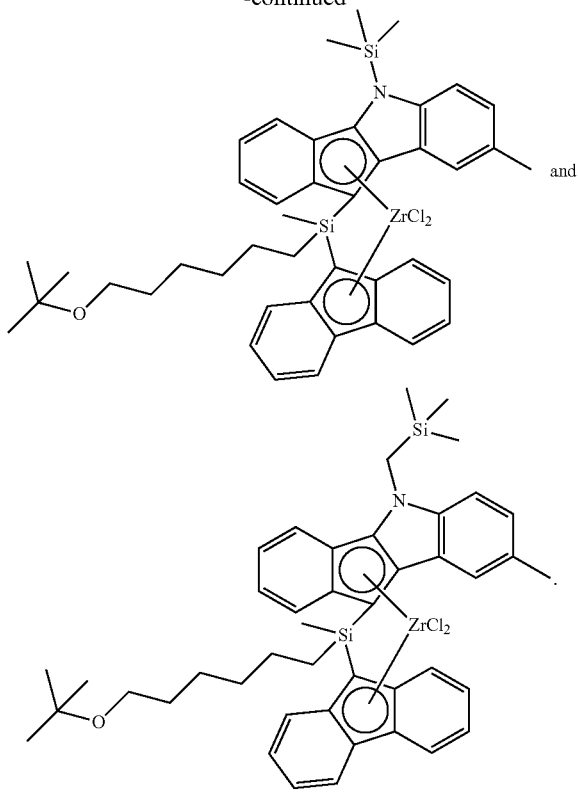

and

9. A catalyst composition, including the metallocene compound of claim 1 and a cocatalyst.

10. The catalyst composition according to claim 9, wherein the cocatalyst includes one or more of the compounds represented by Chemical Formulae 4 to 6:

[Al($R_{18}$)—O]$_n$—      [Chemical Formula 4]

in Chemical Formula 4,
each $R_{18}$ is the same or different, and is independently a halogen; a $C_1$-$C_{20}$ hydrocarbon; or a halogen-substituted $C_1$-$C_{20}$ hydrocarbon; and
n is an integer of 2 or more;

J($R_{18}$)$_3$      [Chemical Formula 5]

in Chemical Formula 5,
$R_{18}$ is same as that in Chemical Formula 4; and
J is aluminum or boron;

[E-H]$^+$[ZA'$_4$]$^-$ or [E]$^+$[ZA'$_4$]$^-$      [Chemical Formula 6]

in Chemical Formula 6,
E is a neutral or cationic Lewis acid;
H is hydrogen atom;
Z is group 13 element; and
each A' is the same or different, and is independently a $C_6$-$C_{20}$ aryl group or a $C_1$-$C_{20}$ alkyl group of which at least one hydrogen atom is unsubstituted or substituted with a halogen, a $C_1$-$C_{20}$ hydrocarbon, an alkoxy, or phenoxy.

11. The catalyst composition according to claim 10, wherein the catalyst is supported on a carrier.

12. The catalyst composition according to claim 11, wherein the carrier is one or more carriers selected from the group consisting of silica, silica-alumina, and silica-magnesia.

13. A method of preparing an olefinic polymer, including the step of polymerizing olefinic monomers in the presence of the catalyst composition according to claim 9.

14. The method of preparing an olefinic polymer according to claim 13, wherein the polymerization reaction is carried out according to a solution polymerization process, slurry process, or a gas phase process.

15. The method of preparing an olefinic polymer according to claim 13, wherein the olefinic monomer is one or more monomers selected from the group consisting of ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, and 1-eicosene.

\* \* \* \* \*